US009883365B2

(12) United States Patent
Kwon et al.

(10) Patent No.: US 9,883,365 B2
(45) Date of Patent: Jan. 30, 2018

(54) MOBILE TERMINAL

(71) Applicant: LG ELECTRONICS INC., Seoul (KR)

(72) Inventors: Yunmi Kwon, Seoul (KR); HongJo Shim, Seoul (KR); Kiseon Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/136,720

(22) Filed: Apr. 22, 2016

(65) Prior Publication Data

US 2016/0381534 A1 Dec. 29, 2016

(30) Foreign Application Priority Data

Jun. 29, 2015 (KR) .......................... 10-2015-0091911

(51) Int. Cl.
*H04W 4/18* (2009.01)
*G01K 13/00* (2006.01)
(Continued)

(52) U.S. Cl.
CPC ............ *H04W 4/18* (2013.01); *A61B 5/0022* (2013.01); *A61B 5/04* (2013.01); *A61B 5/08* (2013.01); *A61B 5/165* (2013.01); *A61B 5/742* (2013.01); *G01K 13/002* (2013.01); *G06F 3/015* (2013.01); *H04M 1/006* (2013.01); *H04M 1/7253* (2013.01); *H04M 1/72569* (2013.01); *H04N 5/23206* (2013.01); *H04N 5/23216* (2013.01); *H04N 5/23293* (2013.01); *H04N 5/247* (2013.01); *H04N 21/4223* (2013.01);
(Continued)

(58) Field of Classification Search
CPC .......... H04W 4/18; H04W 88/02; A61B 5/04; A61B 5/0205; A61B 5/02055; A61B 5/08; A61B 5/021; A61B 5/0022; A61B 5/165; A61B 5/742; H04N 1/00339; H04N 5/23293; H04N 5/23216; H04N 77/147; G06F 3/0488; H04L 51/08
See application file for complete search history.

(56) References Cited

U.S. PATENT DOCUMENTS 8,441,356 B1 5/2013 Tedesco et al.
2004/0208496 A1 10/2004 Pilu
(Continued)

FOREIGN PATENT DOCUMENTS

WO WO 2009/053863 A1 4/2009
WO WO 2014/178044 A1 11/2014

*Primary Examiner* — Thanh Le
(74) *Attorney, Agent, or Firm* — Birch, Stewart, Kolasch & Birch, LLP

(57) ABSTRACT

A wearable mobile terminal including a wireless communication processor configured to provide wireless communication; a display; a sensor configured to sense data including at least one of a heart rate, skin temperature, respiration volume and blood pressure of a first user wearing the mobile terminal; and a controller configured to identify an emotional state of the first user based on the data sensed by the sensor, and control the wireless communication processor to transmit a signal for notifying the emotional state of the first user to at least one or more predetermined external devices, in response to the identified emotional state corresponding to a predetermined emotional state.

12 Claims, 19 Drawing Sheets

(51) Int. Cl.
  G06F 3/01      (2006.01)
  H04M 1/00      (2006.01)
  H04M 1/725     (2006.01)
  A61B 5/04      (2006.01)
  A61B 5/08      (2006.01)
  A61B 5/16      (2006.01)
  H04N 5/232     (2006.01)
  H04N 5/247     (2006.01)
  H04N 21/422    (2011.01)
  H04N 21/4223   (2011.01)
  A61B 5/00      (2006.01)
  A61B 5/0205    (2006.01)
  A61B 5/021     (2006.01)
  H04W 88/02     (2009.01)
  A61B 5/01      (2006.01)
  A61B 5/024     (2006.01)
  A61B 5/0476    (2006.01)
  A61B 5/0488    (2006.01)

(52) U.S. Cl.
  CPC .......... *H04N 21/42201* (2013.01); *A61B 5/01* (2013.01); *A61B 5/021* (2013.01); *A61B 5/024* (2013.01); *A61B 5/0205* (2013.01); *A61B 5/02055* (2013.01); *A61B 5/0476* (2013.01); *A61B 5/0488* (2013.01); *A61B 5/0816* (2013.01); *A61B 5/681* (2013.01); *A61B 5/6803* (2013.01); *A61B 5/6898* (2013.01); *A61B 2562/0219* (2013.01); *G06F 2203/011* (2013.01); *H04M 2250/22* (2013.01); *H04M 2250/52* (2013.01); *H04W 88/02* (2013.01)

(56) References Cited

U.S. PATENT DOCUMENTS

| | | |
|---|---|---|
| 2005/0088296 A1 | 4/2005 | Lee |
| 2012/0004511 A1 | 1/2012 | Sivadas |
| 2014/0192134 A1* | 7/2014 | Jung ............... H04N 7/147 348/14.02 |
| 2014/0192229 A1* | 7/2014 | Kim ............... H04N 1/00339 348/231.3 |
| 2015/0172238 A1* | 6/2015 | Ahmed ............... H04L 51/08 709/217 |
| 2017/0031559 A1* | 2/2017 | Lee ............... G06F 3/0488 |

* cited by examiner

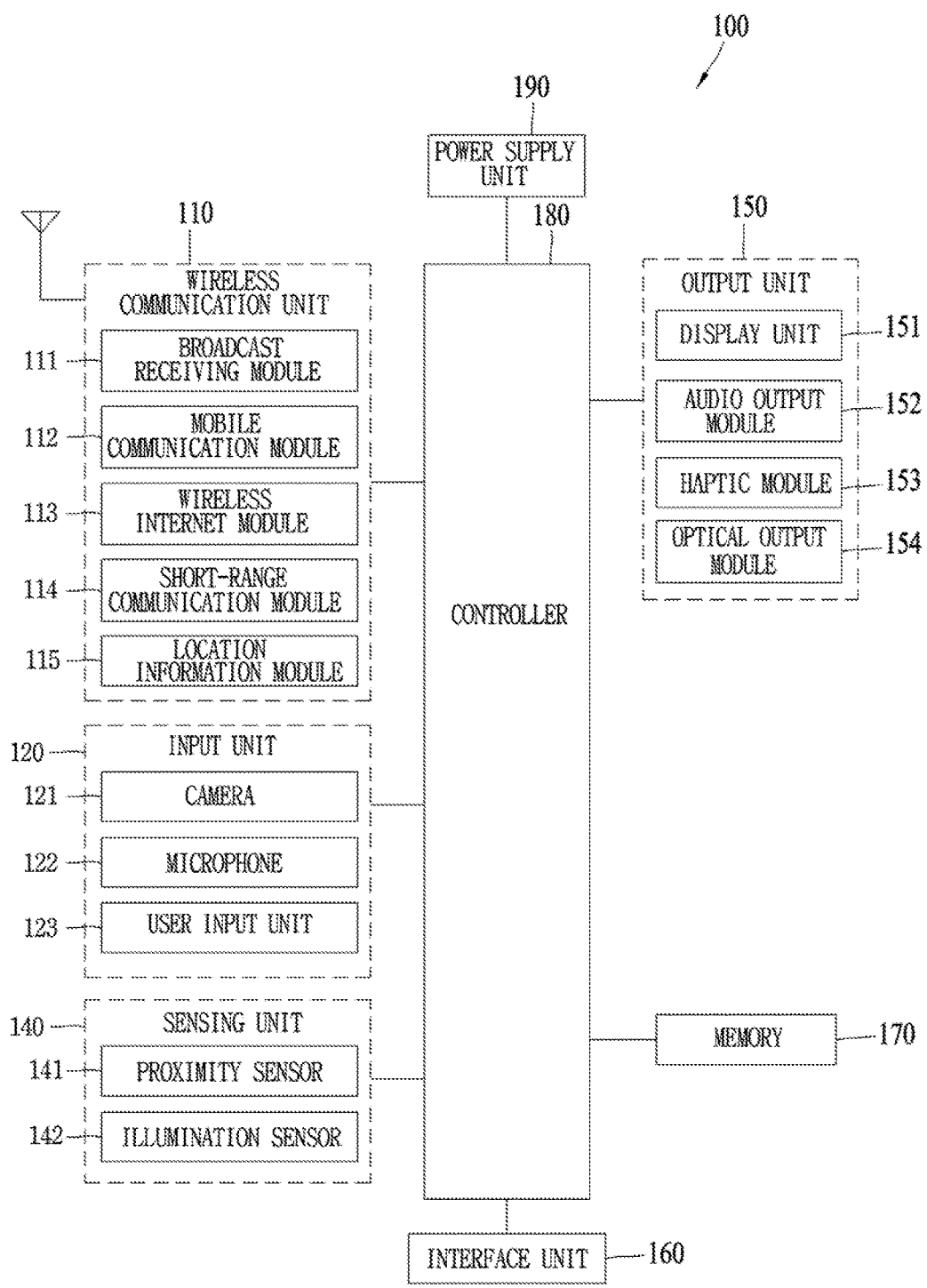

(a)　　　　　　　　　　　　(b)

MOBILE TERMINAL

This application claims priority to Korean Patent Application No. 10-2015-0091911 filed on Jun. 29, 2015 in Korea, the entire contents of which is hereby incorporated by reference in its entirety.

BACKGROUND OF THE INVENTION

Field of the Invention

The present invention relates to a mobile terminal enabling a user to more conveniently use the mobile terminal.

Discussion of the Related Art

Terminals may be generally classified as mobile/portable terminals or stationary terminals. Mobile terminals may also be classified as handheld terminals or vehicle mounted terminals. Mobile terminals have become increasingly more functional. Examples of such functions include data and voice communications, capturing images and video via a camera, recording audio, playing music files via a speaker system, and displaying images and video on a display.

Some mobile terminals include additional functionality which supports game playing, while other terminals are configured as multimedia players. More recently, mobile terminals have been configured to receive broadcast and multicast signals which permit viewing of content such as videos and television programs. Efforts are ongoing to support and increase the functionality of mobile terminals. Such efforts include software and hardware improvements, as well as changes and improvements in the structural components. Further, a band-type or a watch-type mobile terminal is widely disseminated nowadays and can be used to protect children.

SUMMARY OF THE INVENTION

Accordingly, an object of the present invention is to address the above-noted and other problems.

An object of the present invention is to provide a mobile terminal enabling a guardian to take an appropriate action by providing a notification according to emotion of a ward to the guardian.

Another object of the present invention is to provide a mobile terminal enabling a guardian to immediately take a picture of a ward without missing an appearance of the ward when the ward (in particular, children) shows specific emotion.

Still another object of the present invention is to provide a mobile terminal enabling a guardian to easily share a picture of a ward (in particular, children) with a different device.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, according to one embodiment, a mobile terminal includes a sensing unit configured to sense data for at least one of a heart rate, skin temperature, respiration volume and blood pressure of a first user wearing the mobile terminal, a controller configured to identify emotion of the first user based on the data sensed by the sensing unit and a wireless communication unit. In this instance, if the identified emotion corresponds to predetermined emotion, the controller can control the wireless communication unit to transmit a signal for notifying the emotion of the first user to at least one or more predetermined external devices.

To further achieve these objects and other advantages and in accordance with the purpose of the invention, as embodied and broadly described herein, according to a different embodiment, a mobile terminal includes a wireless communication unit configured to receive a first signal for notifying emotion of a user of a first external device from the first external device and a controller configured to display data for notifying the emotion of the user of the first external device on a display unit based on the first signal.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

It is to be understood that both the foregoing general description and the following detailed description of the present invention are exemplary and explanatory and are intended to provide further explanation of the invention as claimed.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 1A is a block diagram of a mobile terminal according to an embodiment of the present disclosure;

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Although the terms first, second, etc. may be used herein to describe various elements, these elements should not be limited by these terms. These terms are generally only used to distinguish one element from another. When an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1B:
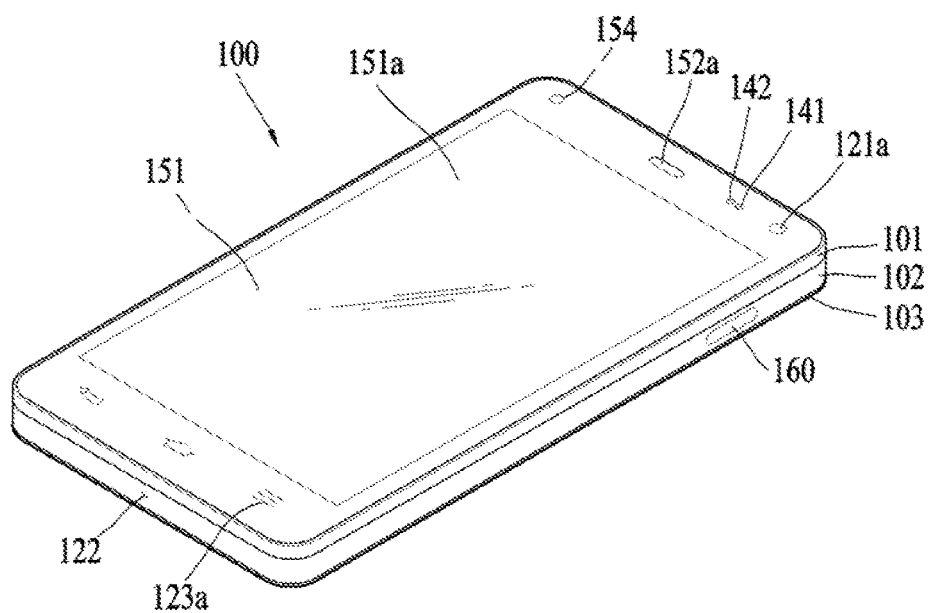
FIGS. 1B and 1C are conceptual views of one example of the mobile terminal, viewed from different directions.
Figure 1C:
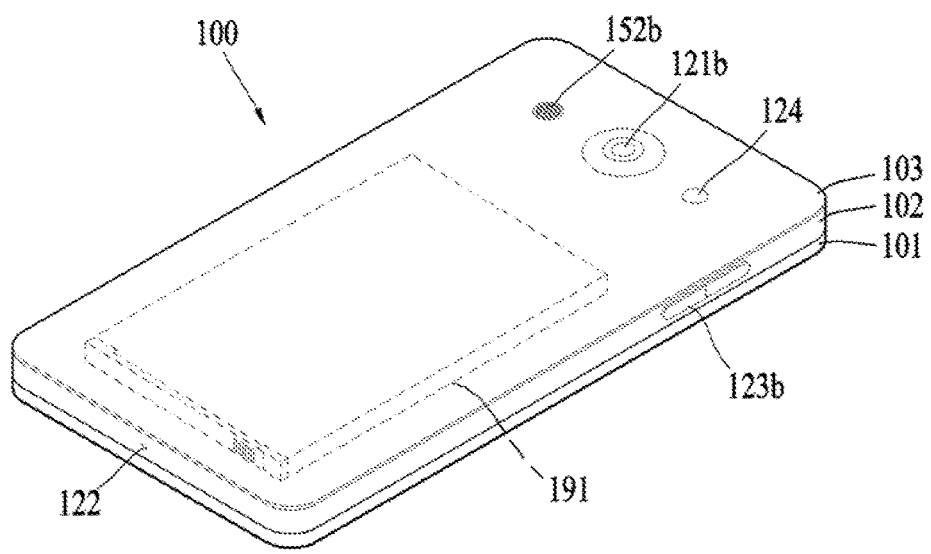

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions. The mobile terminal 100 is shown having components such as a wireless communication unit 110, an input unit 120, a sensing unit 140, an output unit 150, an interface unit 160, a memory 170, a controller 180, and a power supply unit 190. Implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 can provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

A system which generates and transmits a broadcast signal and/or broadcast associated information, or a server which receives a pre-generated broadcast signal and/or broadcast associated information, and sends such items to the mobile terminal. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this instance, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. Further, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 can sense which region of the display unit 151 has been touched. Here, the touch controller may be a component separate from the controller 180, the controller 180, and combinations thereof.

In some embodiments, the controller 180 can execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented so the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 can typically control the general operations of the mobile terminal 100. For example, the controller 180 can set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected. As another example, the power supply unit 190 may be configured to recharge the battery in a wireless manner without use of the connection port.

In this example, the power supply unit 190 can receive power, transferred from an external wireless power transmitter, using at least one of an inductive coupling method which is based on magnetic induction or a magnetic resonance coupling method which is based on electromagnetic resonance. Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like. As an alternative to the example in which the plurality of cases form an inner space for accommodating components, the mobile terminal 100 may be configured such that one case forms the inner space. In this example, a mobile terminal 100 having a uni-body is formed so synthetic resin or metal extends from a side surface to a rear surface.

If desired, the mobile terminal 100 may include a waterproofing unit for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

FIGS. 1B and 1C depict certain components as arranged on the mobile terminal. However, alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a. The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this instance, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof. Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen. As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121*b* is shown located at the rear side of the terminal body and includes an image capturing direction that is substantially opposite to the image capturing direction of the first camera unit 121*a*. If desired, second camera 121*a* may alternatively be located at other locations, or made to be moveable, in order to have a different image capturing direction from that which is shown.

The second camera 121*b* can include a plurality of lenses arranged along at least one line. The plurality of lenses may also be arranged in a matrix configuration. The cameras may be referred to as an "array camera." When the second camera 121*b* is implemented as an array camera, images may be captured in various manners using the plurality of lenses and images with better qualities.

As shown in FIG. 1C, a flash 124 is shown adjacent to the second camera 121*b*. When an image of a subject is captured with the camera 121*b*, the flash 124 may illuminate the subject. As shown in FIG. 1C, the second audio output module 152*b* can be located on the terminal body. The second audio output module 152*b* may implement stereophonic sound functions in conjunction with the first audio output module 152*a*, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Figure 2:
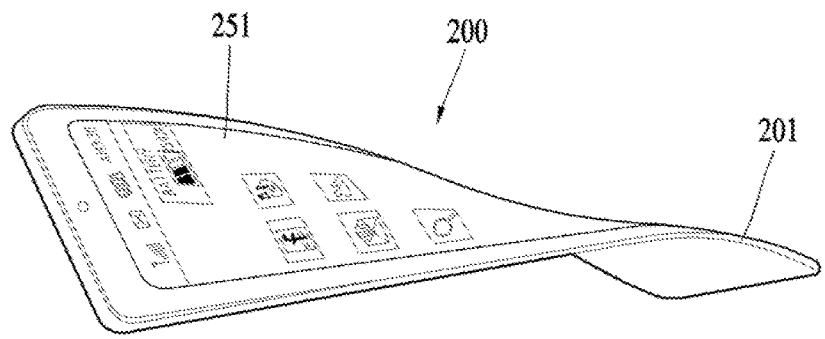
FIG. 2 is a conceptual view of a deformable mobile terminal according to an alternative embodiment of the present disclosure.

FIG. 2 is a conceptual view of a deformable mobile terminal according to an alternative embodiment of the present invention. In this figure, mobile terminal 200 is shown having display unit 251, which is a type of display that is deformable by an external force. This deformation, which includes display unit 251 and other components of mobile terminal 200, may include any of curving, bending, folding, twisting, rolling, and combinations thereof. The deformable display unit 251 may also be referred to as a "flexible display unit." In some implementations, the flexible display unit 251 may include a general flexible display, electronic paper (also known as e-paper), and combinations thereof. In general, mobile terminal 200 may be configured to include features that are the same or similar to that of mobile terminal 100 of FIGS. 1A-1C.

The flexible display of mobile terminal 200 is generally formed as a lightweight, non-fragile display, which still exhibits characteristics of a conventional flat panel display, but is instead fabricated on a flexible substrate which can be deformed as noted previously. The term e-paper may be used to refer to a display technology employing the characteristic of a general ink, and is different from the conventional flat panel display in view of using reflected light. E-paper is generally understood as changing displayed information using a twist ball or via electrophoresis using a capsule.

When the flexible display unit 251 is not deformed (for example, in a state with an infinite radius of curvature and referred to as a first state), a display region of the flexible display unit 251 includes a generally flat surface. When the flexible display unit 251 is deformed from the first state by an external force (for example, a state with a finite radius of curvature and referred to as a second state), the display region may become a curved surface or a bent surface. As illustrated, information displayed in the second state may be visual information output on the curved surface. The visual information may be realized so a light emission of each unit pixel (sub-pixel) arranged in a matrix configuration is controlled independently. The unit pixel denotes an elementary unit for representing one color.

According to one alternative embodiment, the first state of the flexible display unit 251 may be a curved state (for example, a state of being curved from up to down or from right to left), instead of being in flat state. In this embodiment, when an external force is applied to the flexible display unit 251, the flexible display unit 251 may transition to the second state such that the flexible display unit is deformed into the flat state (or a less curved state) or into a more curved state.

If desired, the flexible display unit 251 may implement a flexible touch screen using a touch sensor in combination with the display. When a touch is received at the flexible touch screen, the controller 180 can execute certain control corresponding to the touch input. In general, the flexible touch screen is configured to sense touch and other input while in both the first and second states.

One option is to configure the mobile terminal 200 to include a deformation sensor which senses the deforming of the flexible display unit 251. The deformation sensor may be included in the sensing unit 140.

The deformation sensor may be located in the flexible display unit 251 or the case 201 to sense information related to the deforming of the flexible display unit 251. Examples of such information related to the deforming of the flexible display unit 251 may be a deformed direction, a deformed degree, a deformed position, a deformed amount of time, an acceleration that the deformed flexible display unit 251 is restored, and the like. Other possibilities include most any type of information which can be sensed in response to the curving of the flexible display unit or sensed while the flexible display unit 251 is transitioning into, or existing in, the first and second states.

In some embodiments, controller 180 or other component can change information displayed on the flexible display unit 251, or generate a control signal for controlling a function of the mobile terminal 200, based on the information related to the deforming of the flexible display unit 251. Such information is typically sensed by the deformation sensor.

The mobile terminal 200 is shown having a case 201 for accommodating the flexible display unit 251. The case 201 can be deformable together with the flexible display unit 251, taking into account the characteristics of the flexible display unit 251. A battery located in the mobile terminal 200 may also be deformable in cooperation with the flexible display unit 261, taking into account the characteristic of the flexible display unit 251. One technique to implement such a battery is to use a stack and folding method of stacking battery cells.

The deformation of the flexible display unit 251 not limited to perform by an external force. For example, the flexible display unit 251 can be deformed into the second state from the first state by a user command, application command, or the like. In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 can transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 3:
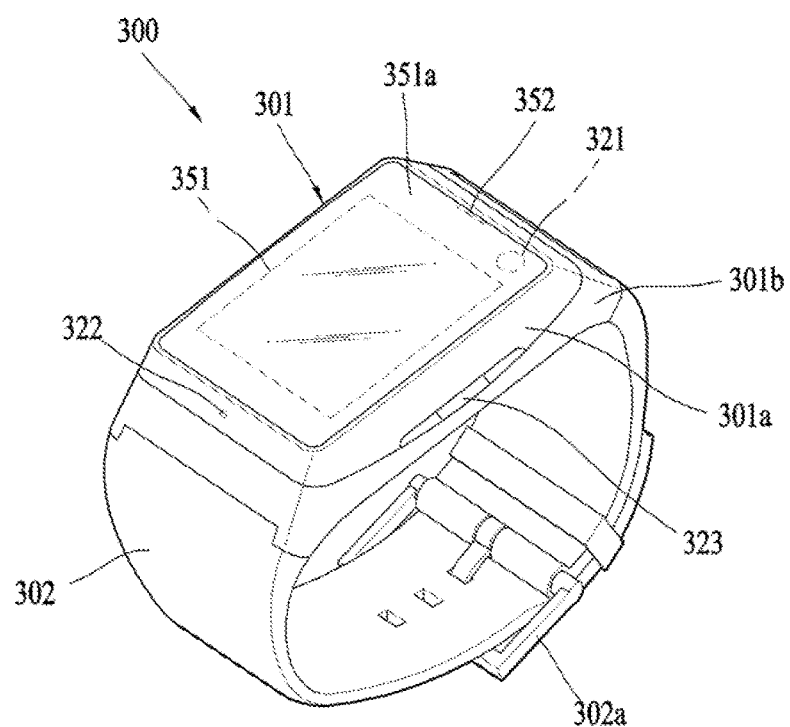
FIG. 3 is a conceptual view of a wearable mobile terminal according to another alternative embodiment of the present disclosure.

FIG. 3 is a perspective view illustrating one example of a watch-type mobile terminal 300 in accordance with another exemplary embodiment. As illustrated in FIG. 3, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion electrically connected to the antenna to extend a ground area. The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

Figure 4:
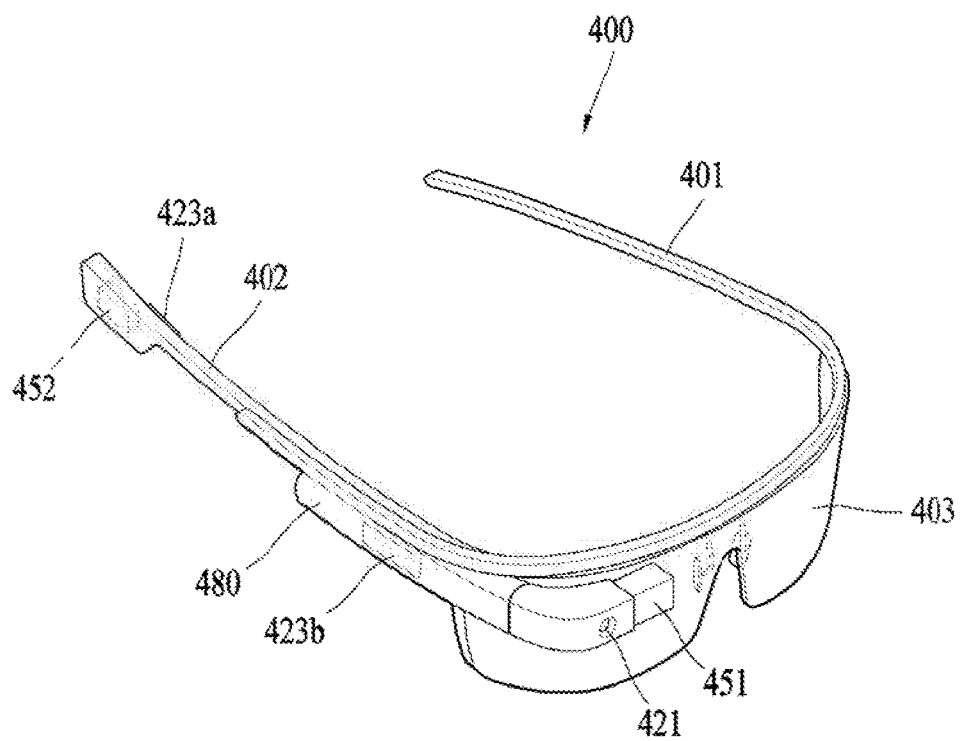
FIG. 4 is a conceptual view of a wearable mobile terminal according to another alternative embodiment of the present disclosure.

FIG. 4 is a perspective view illustrating one example of a glass-type mobile terminal 400 according to another exemplary embodiment. The glass-type mobile terminal 400 can be wearable on a head of a human body and provided with a frame (case, housing, etc.) therefor. The frame may be made of a flexible material to be easily worn. The frame of mobile terminal 400 is shown having a first frame 401 and a second frame 402, which can be made of the same or different materials. In general, mobile terminal 400 may be configured to include features that are the same or similar to that of mobile terminal 100 of FIGS. 1A-1C.

The frame may be supported on the head and defines a space for mounting various components. As illustrated, electronic components, such as a control module 480, an audio output module 452, and the like, may be mounted to the frame part. Also, a lens 403 for covering either or both of the left and right eyes may be detachably coupled to the frame part.

The control module 480 controls various electronic components disposed in the mobile terminal 400. The control module 480 may be understood as a component corresponding to the aforementioned controller 180. FIG. 4 illustrates that the control module 480 is installed in the frame part on one side of the head, but other locations are possible.

The display unit 451 may be implemented as a head mounted display (HMD). The HMD refers to display techniques by which a display is mounted to a head to show an image directly in front of a user's eyes. In order to provide an image directly in front of the user's eyes when the user wears the glass-type mobile terminal 400, the display unit 451 may be located to correspond to either or both of the left and right eyes. FIG. 4 illustrates that the display unit 451 is located on a portion corresponding to the right eye to output an image viewable by the user's right eye.

The display unit 451 may project an image into the user's eye using a prism. Also, the prism may be formed from optically transparent material such that the user can view both the projected image and a general visual field (a range that the user views through the eyes) in front of the user. In such a manner, the image output through the display unit 451 may be viewed while overlapping with the general visual field. The mobile terminal 400 may provide an augmented reality (AR) by overlaying a virtual image on a realistic image or background using the display.

The camera 421 may be located adjacent to either or both of the left and right eyes to capture an image. Since the camera 421 is located adjacent to the eye, the camera 421 can acquire a scene that the user is currently viewing. The camera 421 may be positioned at most any location of the mobile terminal. In some embodiments, multiple cameras 421 may be utilized. Such multiple cameras 421 may be used to acquire a stereoscopic image.

The glass-type mobile terminal 400 may include user input units 423*a* and 423*b*, which can each be manipulated by the user to provide an input. The user input units 423*a* and 423*b* may employ techniques which permit input via a tactile input. Typical tactile inputs include a touch, push, or the like. The user input units 423*a* and 423*b* are shown operable in a pushing manner and a touching manner as they are located on the frame part and the control module 480, respectively.

If desired, mobile terminal 400 may include a microphone which processes input sound into electric audio data, and an audio output module 452 for outputting audio. The audio output module 452 may be configured to produce audio in a general audio output manner or an osteoconductive manner. When the audio output module 452 is implemented in the osteoconductive manner, the audio output module 452 may be closely adhered to the head when the user wears the mobile terminal 400 and vibrate the user's skull to transfer sounds.

A communication system which is operable with the variously described mobile terminals will now be described in more detail. Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system. A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1A is typically configured inside the mobile terminal 100 to receive broadcast signals transmitted by the BT. Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites.

Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module. The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server. The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database. A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter. In addition to these position location methods, various algorithms may be used to extract (analyze) location information of a mobile terminal. Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1A, the mobile terminal may be configured to include short-range communication techniques such as Bluetooth™, Radio Frequency Identification (RFID), Infrared Data Association (IrDA), Ultra Wideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

When the NFC module operates in a card mode, the mobile terminal may transmit card information on a general IC card to the outside. More specifically, if a mobile terminal having card information on a payment card (e.g, a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this instance, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

Further preferred embodiments will be described in more detail with reference to additional drawing figures. It is understood by those skilled in the art that the present features can be embodied in several forms without departing from the characteristics thereof. In the following, embodiments of a method of providing a notification for emotion of a specific person (e.g., a ward) wearing a wearable device to a predetermined third person (e.g., a guardian) are explained with reference to FIG. 5 to FIG. 26.

In the following description, a device (e.g., a device of the ward) providing the notification is called a first mobile terminal 300A/400A and a device (e.g., a device of the guardian) receiving the notification is called a second mobile terminal 100B/200B/300B/400B. Depending on an embodiment, if two or more devices directly or indirectly receive a notification, a further different device may appear. In the embodiment of the present invention, the first mobile terminal 300A/400A may correspond to a mobile terminal of a wearable form and the second mobile terminal 100B/200B/300B/400B may correspond to a mobile terminal of a wearable form or a mobile terminal of a non-wearable form (e.g., it may refer to FIG. 1 and FIG. 2). However, depending on an embodiment, the first mobile terminal may also correspond to the mobile terminal 100A of the wearable form.

Also, in the embodiment of the present invention, a user of the first mobile terminal 300A/400A can be called a first user and a user of the second mobile terminal 100B/200B/300B/400B can be called a second user. Further, in the following description, in case of explaining the embodiments using the mobile terminal of the form mentioned earlier with reference to FIG. 3 and FIG. 4, a configuration module of the mobile terminal 300/400 not depicted in FIG. 3 and FIG. 4 is explained with reference to FIG. 1A.

Figure 5:
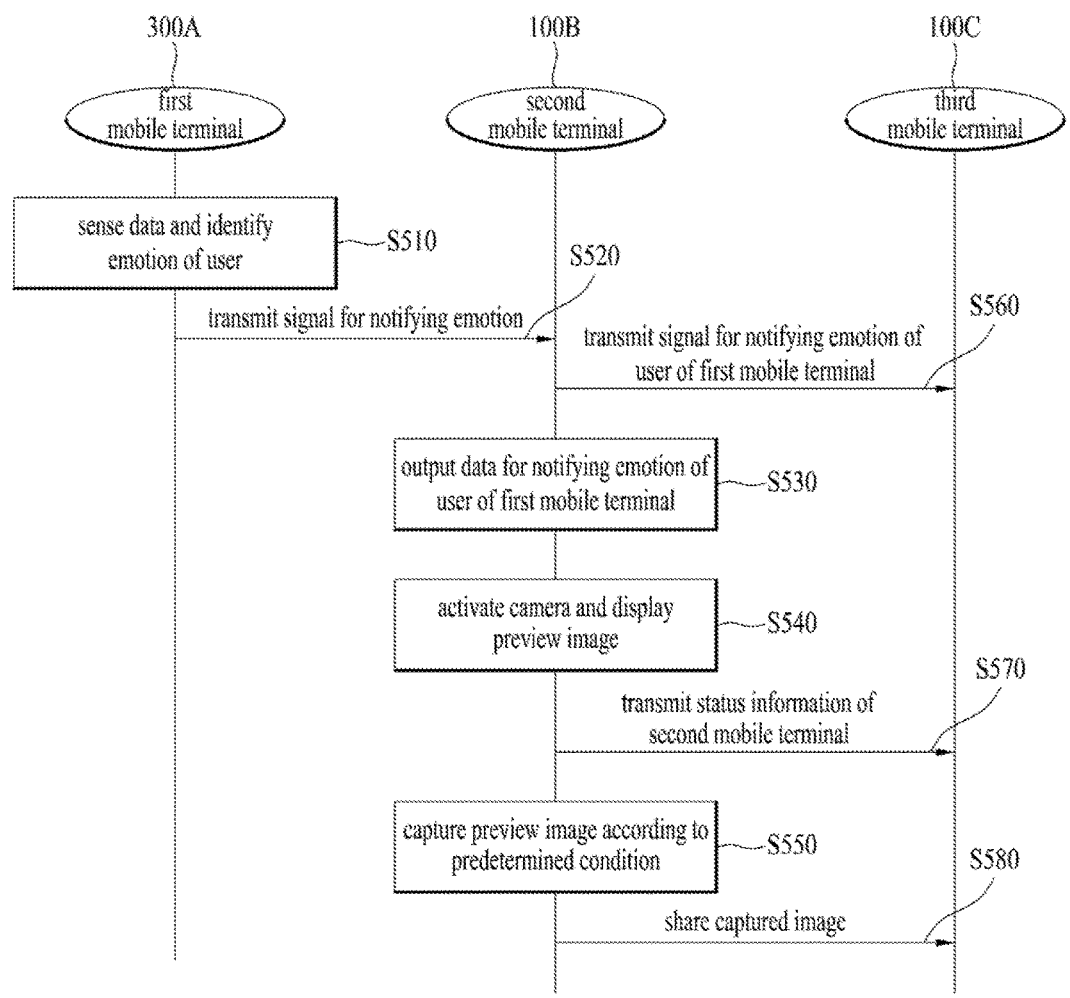
FIG. 5 is a flowchart illustrating a method of providing a notification for emotion of a user of a first mobile terminal to a second mobile terminal according to one embodiment of the present invention.

FIG. 5 is a flowchart illustrating an example of a method of providing a notification for emotion of a user of a first mobile terminal to a second mobile terminal according to one embodiment of the present invention. In the present embodiment, assume that the first mobile terminal 300A corresponds to the mobile terminal mentioned earlier with reference to FIG. 3 and the second mobile terminal 100B and the third mobile terminal 100C correspond to the mobile terminal mentioned earlier with reference to FIG. 1A to FIG. 1C, by which the present invention may be non-limited.

The first mobile terminal 300A senses information of a first user using the sensing unit 140 (S510). For instance, the sensing unit 140 of the first mobile terminal 300 can sense data for at least one of a heart rate of the first user, skin temperature, respiration volume and blood pressure. The sensing unit 140 of the first mobile terminal 300A can include an EMG (electromyography) sensor, an EDA (Electrodermal activity) sensor, an ECG (electrocardiography), a PPG (photoplethysmography) sensor, a GSR (galvanic skin reflex) sensor, a skin temperature sensor and the like. The sensing unit 140 of the first mobile terminal 300 can be mounted on at least a part of the main body 301 and the band 302.

As mentioned earlier with reference to FIG. 4, if the first mobile terminal corresponds to a glass-type or a head-mounted type mobile terminal 400A, the sensing unit 140 can be installed in a frame part. Data sensed by the sensing unit 140 may include brainwave data of the first user. In addition, the controller 180 of the first mobile terminal 300A can determine the emotion (feeling) of the first user based on the data sensed by the sensing unit 140. In particular, the memory 170 of the first mobile terminal 300A can store a program/algorithm for recognizing emotion of a person based on the data sensed by the sensing unit 140 in advance. Specifically, the controller 180 of the first mobile terminal 300A can determine whether the emotion of the first user is positive or negative based on the data sensed by the sensing unit 140.

For instance, if it is determined that a heart rate of the first user is greater than a predetermined level, the skin temperature of the first user is greater than a predetermined level, a stress quotient of the first user is greater than a predetermined level and the respiration volume of the first user is greater than a predetermined level based on the data sensed by the sensing unit 140, the controller 180 of the first mobile terminal 300A can determine the first user is in a state of being mad. As an example, the stress quotient can be deducted by utilizing HRV (heart rate variability) data based on data sensed by the PPG sensor and/or the ECG sensor.

If it is determined that the heart rate of the first user is greater than the predetermined level, the skin temperature of the first user is greater than the predetermined level, the stress quotient of the first user is greater than the predetermined level and the respiration volume of the first user is less than the predetermined level based on the data sensed by the sensing unit 140, the controller 180 of the first mobile terminal 300A can determine the first user is in a state of feeling fear.

If it is determined that the heart rate of the first user is less than the predetermined level, a change of the skin temperature of the first user is maintained within the predetermined level, the stress quotient of the first user is less than the predetermined level and the respiration volume of the first user is less than the predetermined level based on the data sensed by the sensing unit 140, the controller 180 of the first mobile terminal 300A can determine the first user is in a state of pleasant or happy.

The controller 180 of the first mobile terminal 300A controls the wireless communication unit 110 to transmit a first signal for notifying the identified emotion (emotional state) of the first user to a predetermined second mobile terminal 100B (S520). The first signal can include information on the first mobile terminal 300A, information on the first user, information on the emotion of the first user and the like. The controller 180 of the first mobile terminal 300A can also transmit the first signal to a plurality of predetermined mobile terminals, respectively. In the present embodiment, the wireless communication unit 110 corresponds to at least one of the mobile communication module 112, the wireless internet module 113 and the short range communication module 114.

The controller 180 of the second mobile terminal 100B receives the first signal via the wireless communication unit 110 and can output data for notifying the emotion of the first user (S530). The controller 180 of the second mobile terminal 100B can output the data for notifying the emotion of the first user through at least one of the display unit 151, the audio output module 152, the haptic module 153 and the optical output module 154 according to a type of the output data. As an example, the controller 180 of the second mobile terminal 100B can display a notification message for notifying a current emotional state of the first user on the display unit 151.

The controller 180 of the second mobile terminal 100B activates the camera 121 in response to the first signal and can display a preview image captured by the activated camera 121 on the display unit 151 (S540). According to the present embodiment, if the first user (i.e., a child) shows a specific emotion, the camera 121 of the second mobile terminal 100B of the second user (i.e., a guardian) is automatically activated and can take a picture of a natural appearance of the first user.

Further, the controller 180 of the second mobile terminal 100B can control the camera 121 to capture the preview image according to a predetermined condition without a capture command of a user (S550). Specifically, the sensing unit 140 of the second mobile terminal 100B can obtain information (information on at least one of movement and a slope) of the second mobile terminal 100B. In addition, if the second mobile terminal 100B satisfies a predetermined condition, the controller 180 of the second mobile terminal 100B can control the camera 121 to capture the preview image based on the received first signal and the data sensed by the sensing unit 140. As an example, the predetermined condition may include that a value of data for the movement of the second mobile terminal 100B sensed by the sensing unit 140 is within a predetermined range when the second mobile terminal 100B faces a direction to which the first signal is transmitted.

Further, the controller 180 of the second mobile terminal 100B can control the wireless communication unit 110 to transmit the received first signal to a predetermined third mobile terminal 100C (S560). For example, if it is determined that the second mobile terminal is positioned at a specific place, a specific application is executed or a notification mode of the second mobile terminal 100B is set to a manner mode or a silent mode based on information obtained by the location information module 115 at the time of receiving the first signal, the controller 180 of the second mobile terminal 100B can deliver the received first signal to the predetermined third mobile terminal 100C. In this instance, the second mobile terminal 100B may provide no notification to a second user in relation to the reception of the first signal.

Alternatively, the second mobile terminal 100C can separately receive the first signal from the first mobile terminal 300A. Further, if the camera 121 is activated in response to the first signal, the controller 180 of the second mobile terminal 100B can control the wireless communication unit 110 to transmit a second signal including status information of the second mobile terminal 100B to the predetermined third mobile terminal 100C (S570). As an example, the status information of the second mobile terminal 100B can include implementation information of the camera 121 of the second mobile terminal 100B.

Further, if an image is captured by the camera 121, the controller 180 of the second mobile terminal 100B can control the wireless communication unit 110 to transmit the captured image to the predetermined third mobile terminal 100C (S580).

Figure 6:
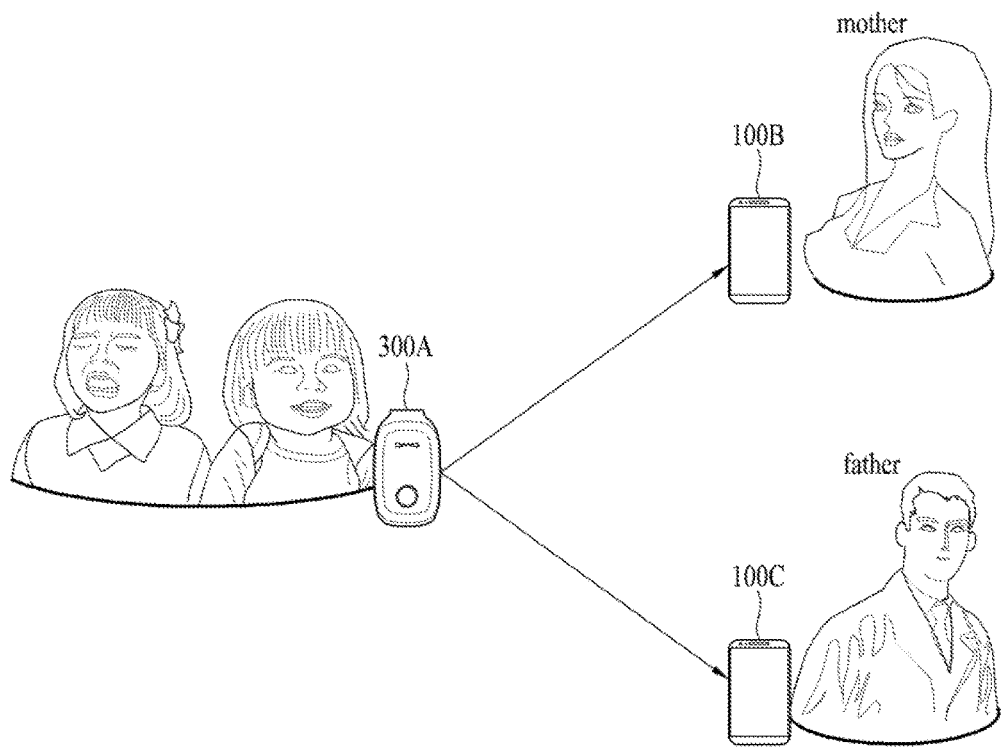
FIG. 6 is a diagram illustrating a method of notifying emotion of a user of a first mobile terminal to a predetermined external device according to one embodiment of the present invention.

Next, FIG. 6 is a diagram illustrating a method of notifying an emotion of a user of a first mobile terminal to a predetermined external device according to one embodiment of the present invention.

The controller 180 of the first mobile terminal 300A recognizes emotion of a first user based on data sensed by the sensing unit 140. If the recognized emotion of the first user corresponds to a predetermined emotion (e.g., sad emotion and pleasant emotion), the controller 180 of the first mobile terminal 300A can control the wireless communication unit 110 to transmit a first signal for notifying the emotion of the first user to the predetermined second mobile terminal 100B and the third mobile terminal 100C. The first mobile terminal 300A can also transmit the first signal to a single external device or three or more external devices. In addition, an external device receiving the first signal can be configured by the first user or a user of the external device.

The controller 180 of the first mobile terminal 300A transmits a prescribed signal to the first mobile terminal 300A before the first signal is transmitted to the second mobile terminal 100B and the third mobile terminal 100C and can detect a distance from the second mobile terminal 100B and a distance from the third mobile terminal 100C in response to the signal based on a second signal transmitted from the second mobile terminal 100B and the third mobile terminal 100C. In addition, the controller 180 of the first mobile terminal 300A can control the wireless communication unit 110 to transmit the first signal to the mobile terminal (100B or 100C) of which the detected distance is shorter among the second mobile terminal 100B and the third mobile terminal 100C.

For instance, the distance from the second mobile terminal 100B and the distance from the third mobile terminal 100C can be detected using a delay level of a signal respectively transceived with the second mobile terminal 100B and the third mobile terminal 100C, a strength of a signal respectively transmitted from the second mobile terminal 100B and the third mobile terminal 100C, location information respectively transmitted from the second mobile terminal 100B and the third mobile terminal 100C and the like.

Figure 7:
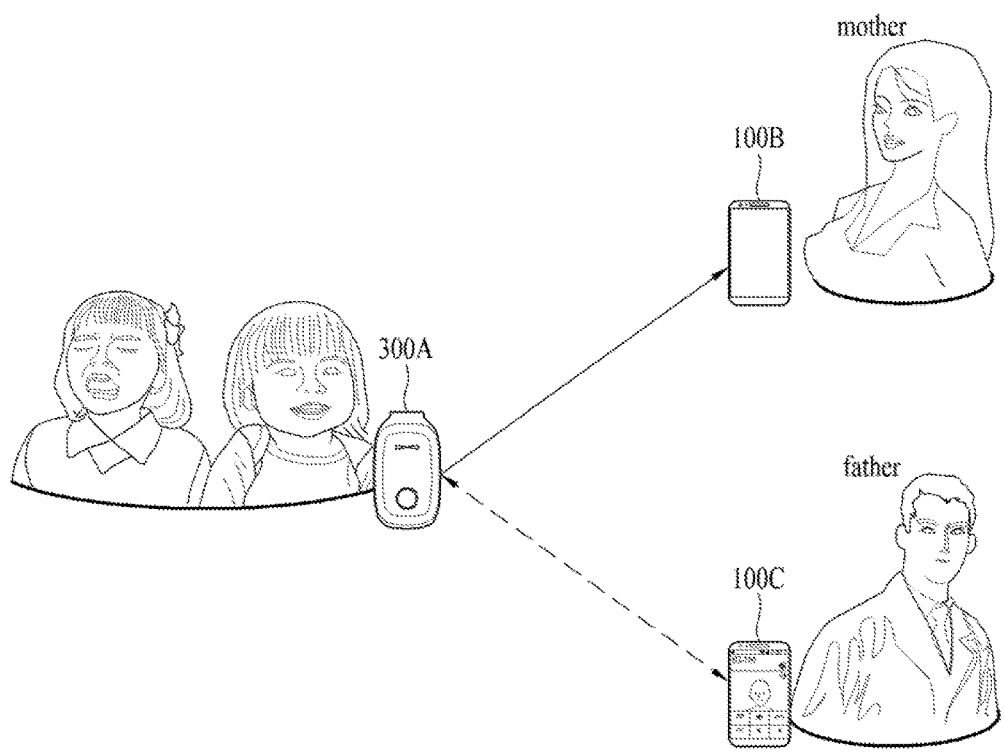
FIG. 7 is a diagram illustrating a method of notifying emotion of a user of a first mobile terminal to a predetermined external device according to another embodiment of the present invention.

FIG. 7 is a diagram illustrating a method of notifying an emotion of a user of a first mobile terminal to a predetermined external device according to another embodiment of the present invention. The controller 180 of the first mobile terminal 300A recognizes the emotion of a first user based on data sensed by the sensing unit 140. If the recognized emotion of the first user corresponds to a predetermined emotion (e.g., sad emotion and pleasant emotion), the controller 180 of the first mobile terminal 300A can control the wireless communication unit 110 to transmit a first signal for notifying the emotion of the first user to at least one of a predetermined second mobile terminal 100B and a third mobile terminal 100C.

In the present embodiment, assume that a predetermined application is currently executed in the third mobile terminal 100C. For instance, the predetermined application may correspond to a phone call application, a video playback application, a DMB application or the like. The controller 180 of the first mobile terminal 300A transmits a prescribed signal to the second mobile terminal 100B and the third mobile terminal 100C before the first signal is transmitted to at least one of the second mobile terminal 100B and the third mobile terminal 100C and can control the wireless communication unit 110 to receive information on a status of a mobile terminal from the second mobile terminal 100B and the third mobile terminal 100C, respectively.

The second mobile terminal 100B and the third mobile terminal 100C can transmit status information on whether it is feasible to receive a notification for the emotion of the first user or status information on whether is not feasible to receive a notification for the emotion of the first user due to the execution of the predetermined application to the first mobile terminal 300A.

If the status information indicating that it is feasible to receive the notification for the emotion of the first user is received from the second mobile terminal 100B, the controller 180 of the first mobile terminal 300A can transmit the first signal to the second mobile terminal 100B via the wireless communication unit 110. Further, if the status information indicating that it is not feasible to receive the notification for the emotion of the first user is received from the third mobile terminal 100C, the controller 180 of the first mobile terminal 300A may not transmit the first signal to the third mobile terminal 100C.

According to the present embodiment, if a user of an external device, which is configured to receive a notification for the emotion of a first user, currently uses a predetermined application (e.g., phone call application) using the external device, the notification for the emotion of the first user is not provided to the user in order not to interrupt the use of the predetermined application.

Figure 8:
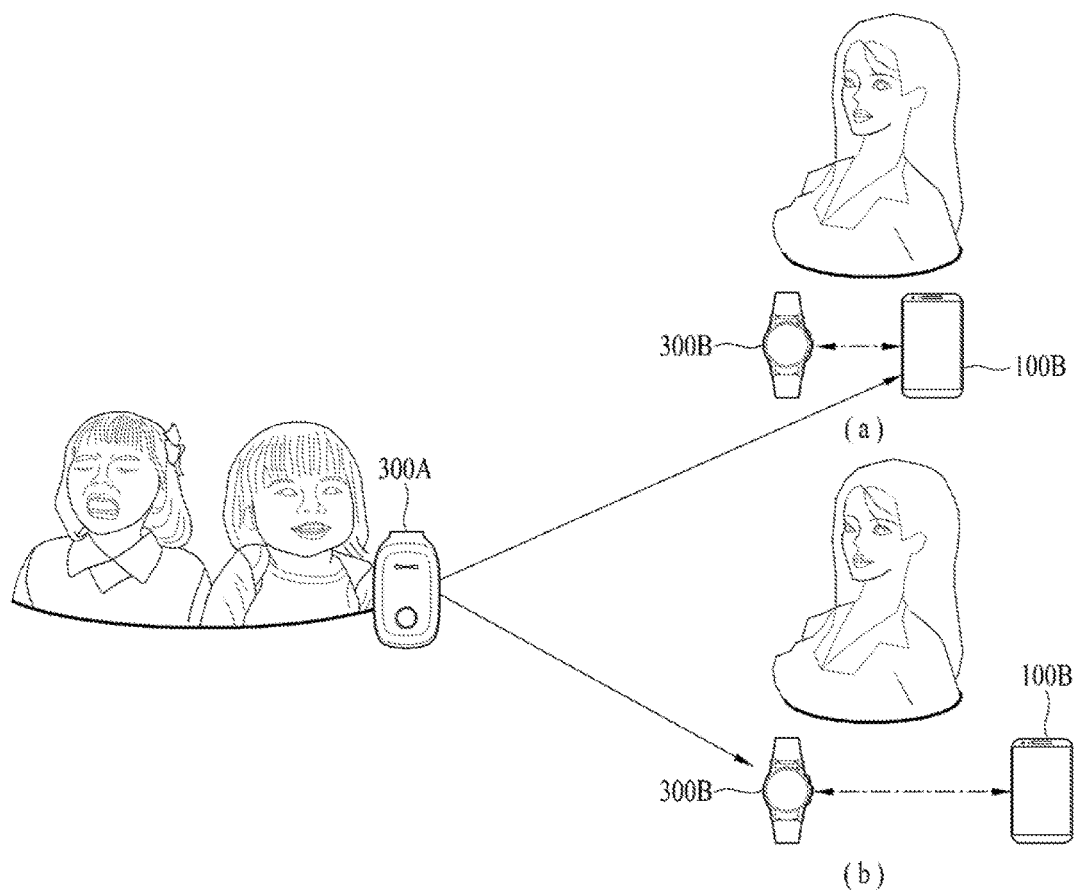
FIG. 8 is a diagram illustrating a method of notifying emotion of a user of a first mobile terminal to a predetermined external device according to still another embodiment of the present invention.

Next, FIG. 8 is a diagram illustrating a method of notifying emotion of a user of a first mobile terminal to a predetermined external device according to still another embodiment of the present invention.

The controller 180 of the first mobile terminal 300A recognizes the emotion of a first user based on data sensed by the sensing unit 140. If the recognized emotion of the first user corresponds to a predetermined emotion (e.g., sad emotion and pleasant emotion), the controller 180 of the first mobile terminal 300A can control the wireless communication unit 110 to transmit a first signal for notifying the emotion of the first user to at least one of a predetermined second mobile terminal 100B and a third mobile terminal 300B.

In the present embodiment, assume that the second mobile terminal 100B and the third mobile terminal 300B are devices corresponding to an identical second user and the second user is wearing the third mobile terminal 300B of a wearable type. The first mobile terminal 300A may be aware of information on the second user of the second mobile terminal 100B and the third mobile terminal 300B, information on a device form of each of the second mobile terminal 100B and the third mobile terminal 300B and information on whether the third mobile terminal 300B of the wearable form is worn on the second user. In this instance, the information on the device form may include information indicating whether the second mobile terminal 100B and the third mobile terminal 300B correspond to devices of a wearable form or devices of a non-wearable form.

The controller 180 of the first mobile terminal 100A can receive first information necessary for recognizing a distance between the second mobile terminal 100B and the third mobile terminal 300C from at least one of the second mobile terminal 100B and the third mobile terminal 300C before the first signal is transmitted to at least one of the second mobile terminal 100B and the third mobile terminal 300C.

As an example, the controller 180 of the first mobile terminal 100A recognize a distance to the second mobile terminal 100B and a distance to the third mobile terminal 300B based on a signal respectively received from the predetermined second mobile terminal 100B and the third mobile terminal 300B and can then infer a distance between the second mobile terminal 100B and the third mobile terminal 300B from the distance to the second mobile terminal 100B and the distance to the third mobile terminal 300B.

As a different example, at least one of the second mobile terminal 100B and the third mobile terminal 100C recognizes a mutual distance based on a signal transceived between the second mobile terminal 100B and the third mobile terminal 100C and can transmit information on the distance between the second mobile terminal 100B and the third mobile terminal 100C to the first mobile terminal 300A.

As an example, referring to FIG. 8 (a), if the distance between the second mobile terminal 100B and the third mobile terminal 100C is less than a predetermined level, the controller 180 of the first mobile terminal 100A transmits the first signal to the second mobile terminal 100B of the non-wearable type among the second mobile terminal 100B and the third mobile terminal 100C and does not transmit the first signal to the third mobile terminal 100C of the wearable type.

That is, if the distance between the second mobile terminal 100B and the third mobile terminal 100C is less than the predetermined level, the second user can be determined as carrying both the second mobile terminal 100B and the third mobile terminal 100C. In this instance, a notification for the emotion of the first user can be provided to the second mobile terminal 100B of the non-wearable type only. This is because the second mobile terminal 100B of the non-wearable type, which is convenient for immediately capturing a picture in response to the notification for the emotion of the first user, can match up to an intention of the user.

Alternatively, if the distance between the second mobile terminal 100E and the third mobile terminal 100C is less than the predetermined level, the controller 180 of the first mobile terminal 100A can transmit the first signal to both the second mobile terminal 100B and the third mobile terminal 100C. In this instance, the second mobile terminal 100B outputs visual data for notifying the emotion of the first user in the display unit according to the first signal and the third mobile terminal 300B may output vibration data for notifying the emotion of the first user to the haptic module 153 according to the first signal. In particular, a vibration notification can be provided to the third mobile terminal 300B of the wearable type only and information specifically notifying the emotion of the first user can be provided to the second user via the second mobile terminal 100B.

Further, as a different example, referring to FIG. 8 (b), if the distance between the second mobile terminal 100B and the third mobile terminal 100C is greater than the predetermined level, the controller 180 of the first mobile terminal 100A transmits the first signal to the third mobile terminal 300B and does not transmit the first signal to the second mobile terminal 100C of the non-wearable type. When the distance between the second mobile terminal 100B and the third mobile terminal 100C is greater than the predetermined level, since the third mobile terminal 100C is currently worn on the second user, the second mobile terminal 100B is determined as not currently carried by the second user. In this instance, it the notification for the emotion of the first user can be provided to the third mobile terminal 300B carried by the second user only.

Figure 9:
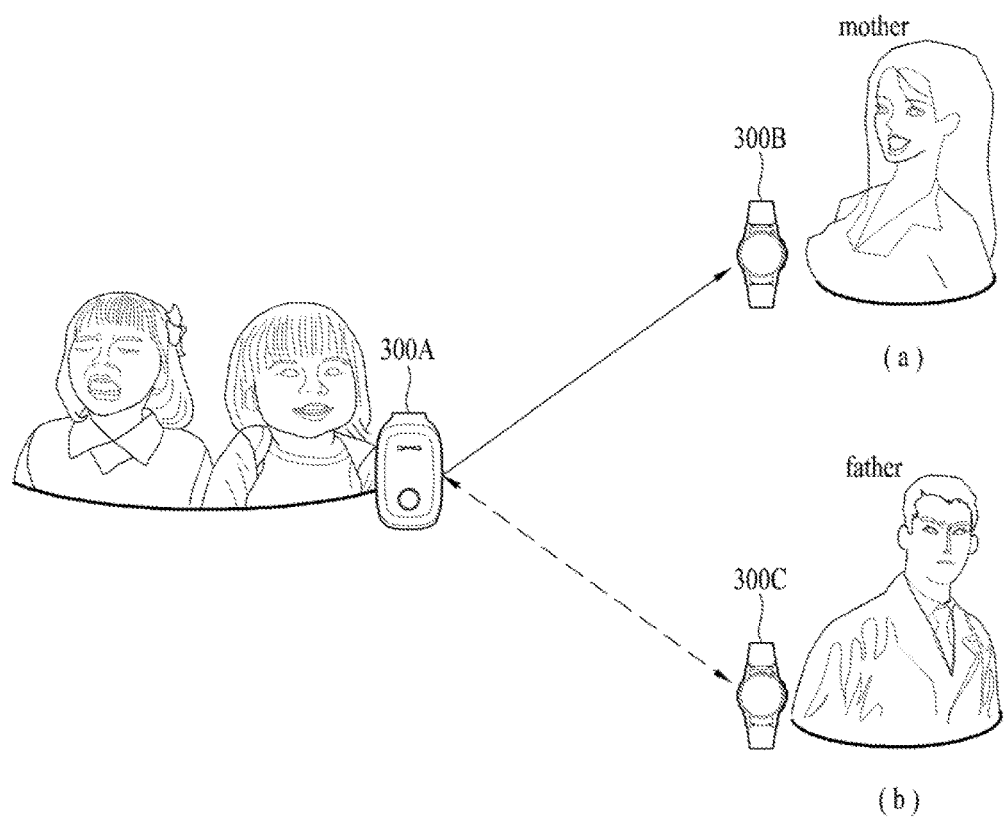
FIG. 9 is a diagram illustrating a method of notifying emotion of a user of a first mobile terminal to a predetermined external device according to one embodiment of the present invention.

Next, FIG. 9 is a diagram illustrating a method of notifying an emotion of a user of a first mobile terminal to a predetermined external device according to one embodiment of the present invention.

The controller 180 of the first mobile terminal 300A recognizes the emotion of a first user based on data sensed by the sensing unit 140. If the recognized emotion of the first user corresponds to a predetermined emotion (e.g., sad emotion and pleasant emotion), the controller 180 of the first mobile terminal 300A can control the wireless communication unit 110 to transmit a first signal for notifying the emotion of the first user to at least one of a predetermined second mobile terminal 100B and a third mobile terminal 100C.

In the present embodiment, assume that the second mobile terminal 300B and the third mobile terminal 300C correspond to a mobile terminal of a wearable form (e.g., a watch-type or a glass-type mobile terminal). The controller 180 of the first mobile terminal 300A can control the wireless communication unit 110 to transmit a prescribed signal to the second mobile terminal 300B and the third mobile terminal 300C and receive a second signal including information on emotion of each user (a second user of the second mobile terminal 100B and a third user of the third mobile terminal 300B) from the second mobile terminal 300B and the third mobile terminal 300C before the first signal is transmitted to at least one of the predetermined second mobile terminal 300B and the third mobile terminal 300C. The controller 180 of the second mobile terminal 300B and the controller of the third mobile terminal 300C can recognize the emotion of each user based on data sensed by the sensing unit 140.

The controller 180 of the first mobile terminal 300A can control the wireless communication unit 110 to transmit the first signal to a mobile terminal of which the emotion of the user corresponds to a predetermined emotion among the second mobile terminal 300B and the third mobile terminal 300C based on the information included in the second signal respectively received from the second mobile terminal 300B and the third mobile terminal 300C.

As an example, referring to FIG. 9 (a), if emotion of the second user corresponds to predetermined first emotion (e.g., pleasant emotion, happy emotion etc.), the controller 180 of the first mobile terminal 300A can transmit the first signal to the second mobile terminal 300B via the wireless communication unit 110 based on the information included in the second signal received from the second mobile terminal 300B.

As a different example, referring to FIG. 9 (b), if emotion of the third user corresponds to predetermined second emotion (e.g., angry emotion, sad emotion etc.), the controller 180 of the first mobile terminal 300A may not transmit the first signal to the third mobile terminal 300C based on the information included in the second signal received from the third mobile terminal 300C.

The controller 180 of the first mobile terminal 300A receives location information from the second mobile terminal 100B and the third mobile terminal 300C and may not transmit the first signal to a mobile terminal located at a predetermined location (e.g., a company, a library, etc.) among the second mobile terminal 100B and the third mobile terminal 100C based on the received location information.

According to the present embodiment, providing a notification to a user of an external device configured to receive the notification for emotion of a first user according to emotion/situation of the user of the external device more precisely matches to an intention of the user.

Figure 10:
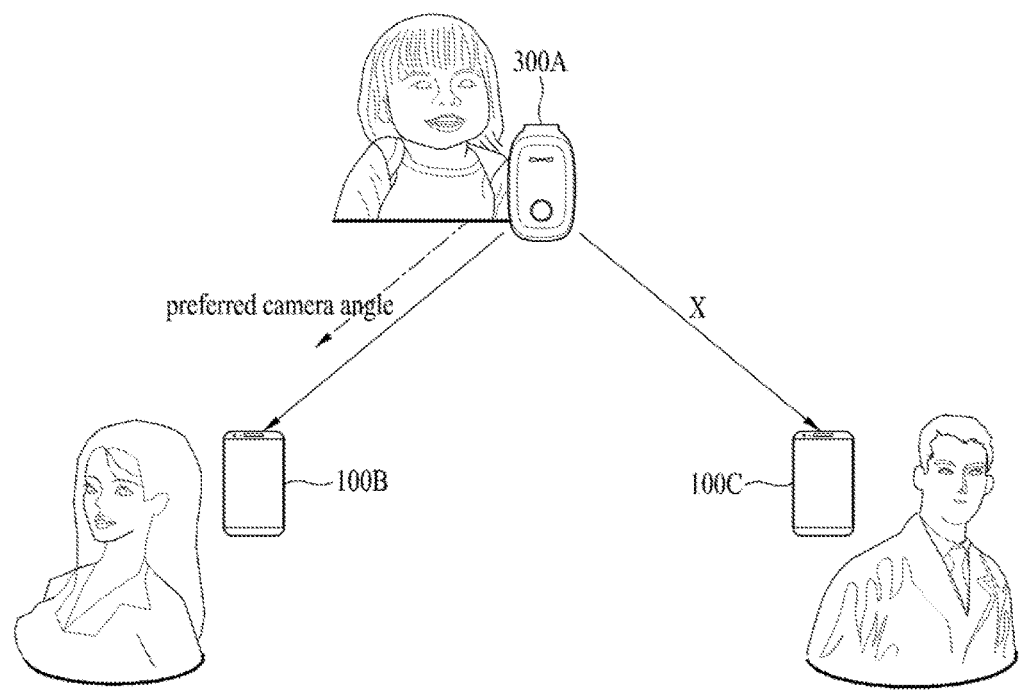
FIG. 10 is a diagram illustrating a method of notifying emotion of a user of a first mobile terminal to a predetermined external device according to another embodiment of the present invention.

Next, FIG. 10 is a diagram illustrating a method of notifying an emotion of a user of a first mobile terminal to a predetermined external device according to one embodiment of the present invention. The controller 180 of the first mobile terminal 300A recognizes the emotion of a first user based on data sensed by the sensing unit 140. If the recognized emotion of the first user corresponds to a predetermined emotion (e.g., sad emotion and pleasant emotion), the controller 180 of the first mobile terminal 300A can control the wireless communication unit 110 to transmit a first signal for notifying the emotion of the first user to at least one of a predetermined second mobile terminal 100B and a third mobile terminal 100C.

The controller 180 of the first mobile terminal 100A transmits a prescribed signal to the second mobile terminal 100B and the third mobile terminal 100C and can receive a second signal in response to the signal before the first signal is transmitted to at least one of the second mobile terminal 100B and the third mobile terminal 100C. The controller 180 of the first mobile terminal 100A can detect a direction at which each of the second mobile terminal 100B and the third mobile terminal 300C is located based on the first mobile terminal 100A based on the received second signal. In addition, the controller 180 of the first mobile terminal 100A can control the wireless communication unit 110 to transit the first signal to a mobile terminal (e.g., the second mobile terminal 100B) located at predetermined direction among the second mobile terminal 100B and the third mobile terminal 300C.

For instance, the predetermined direction may correspond to a camera angle preferred by the first user. The predetermined direction can be configured by the first user or a user of an external device (e.g., the second mobile terminal 100B and the third mobile terminal 100C). Alternatively, the predetermined direction can be automatically configured in a manner that the controller 180 of the first mobile terminal 300A analyzes pictures of the first user stored in the memory 170 and detects direction in which the first user is mainly captured.

In the following, examples of a method for an external device, which has received notification for emotion of a first user, to output the notification to a user are explained with reference to FIG. 11 to FIG. 14. In particular, FIG. 11 is a diagram illustrating a second mobile terminal, which has received notification for the emotion of the first user from the first mobile terminal, according to one embodiment of the present invention.

In the present embodiment, assume that the second mobile terminal 100B receives the first signal for notifying an emotion of the first user from the first mobile terminal 300A. However, it is apparent that a device except the second mobile terminal 100B can receive the first signal. The controller 180 of the second mobile terminal 100B can output data for notifying the emotion of the first user on the display unit 151 based on the received first signal.

Figure 11:
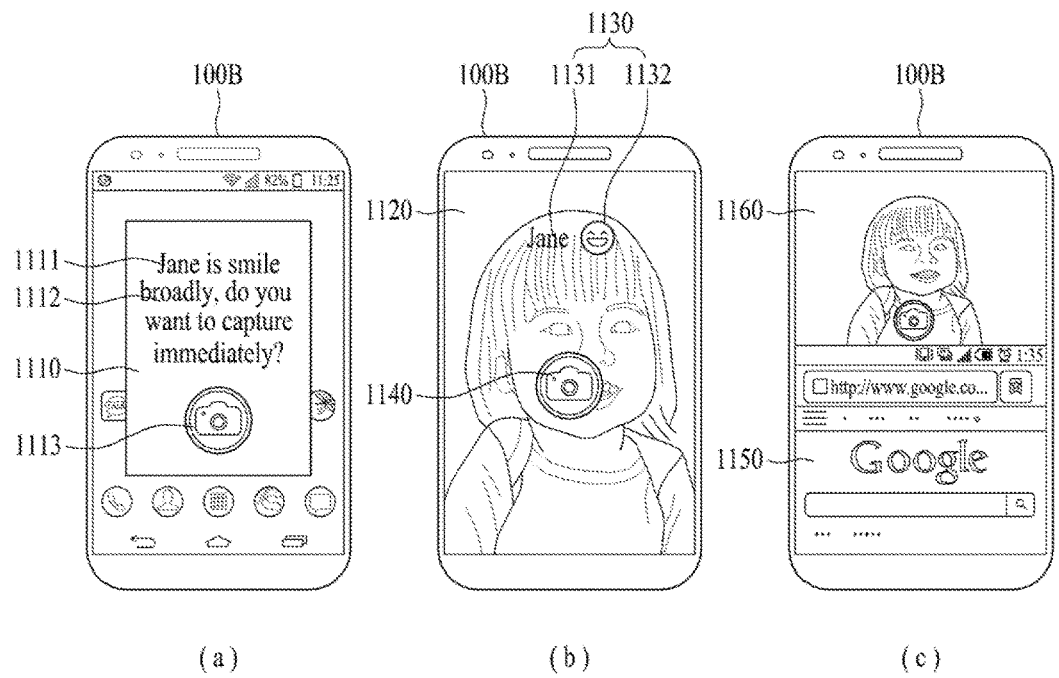
FIG. 11 is a diagram illustrating a second mobile terminal, which has received notification for emotion of a first user from a first mobile terminal, according to one embodiment of the present invention.

As an example, referring to FIG. 11 (a), the controller 180 of the second mobile terminal 100B can display a pop-up message 1110 for notifying the emotion of the first user on the display unit 151 in response to the received first signal. The pop-up message 1110 can include at least one of information 1111 for identifying the first user, information 1112 indicating the emotion of the first user and a camera UI 1113 for taking a picture of the first user. The controller 180 of the second mobile terminal 100B activates the camera 121 according to a command for selecting the camera UI 1113 and can display a preview image obtained by the camera 121 on the display unit 151.

As a different example, referring to FIG. 11 (b), the controller 180 of the second mobile terminal 100B activates the camera 121 in response to the received first signal and outputs a preview image 1120 obtained by the activated camera 121 on the display unit 151. The controller 180 of the second mobile terminal 100B can display information 1130 corresponding to the first user on the preview image 1120. For example, the information 1130 corresponding to the first user can include at least one of information 1131 for identifying the first user and information 1132 indicating the emotion of the first user. In addition, the controller 180 of the second mobile terminal 100B can display a capture command UI 1140 corresponding to a capture command on the preview image 1120. The controller 180 of the second mobile terminal 100B can capture the preview image 1120 according to a command for selecting the capture command UI 1140.

As a further different example, referring to FIG. 11 (c), if the first signal is received in the middle of executing an application, the controller 180 of the second mobile terminal 100B displays an execution screen of the application on a first area 1150 of the display unit 151 and can display data for notifying the emotion of the first user on a second area 1160 of the display unit 151. The data displayed on the second area 1160 is similar to what is mentioned earlier with reference to FIGS. 11 (a) and (b). If a signal for notifying the emotion of the first user is received, a second user of the second mobile terminal 100B can determine a type and a form of data to be displayed on the display unit 151 in advance.

Figure 12:
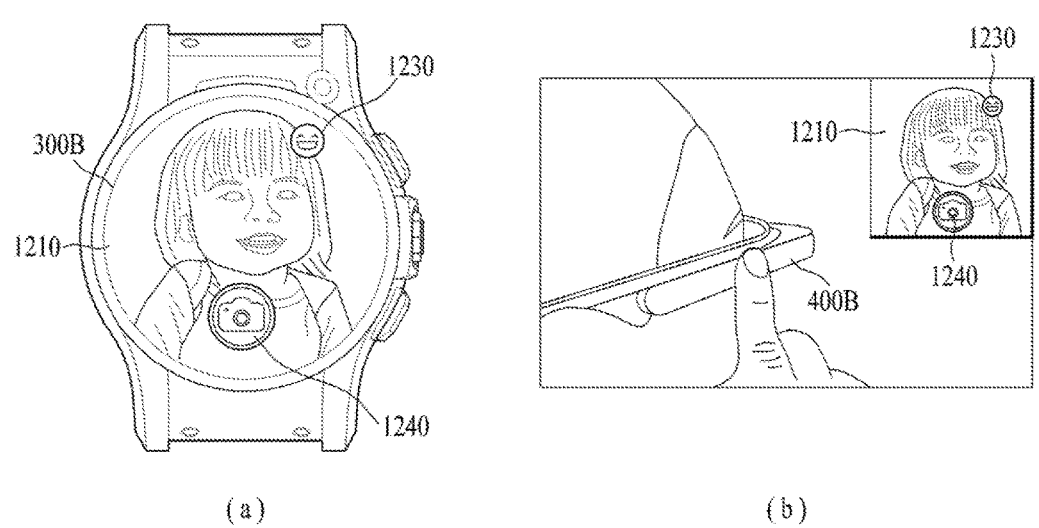
FIG. 12 is a diagram illustrating a second mobile terminal, which has received notification for emotion of a first user from a first mobile terminal, according to another embodiment of the present invention.

FIG. 12 is a diagram illustrating a second mobile terminal, which has received notification for emotion of a first user from a first mobile terminal, according to another embodiment of the present invention. In the present embodiment, assume that a second mobile terminal 300B or a second mobile terminal 400B receives the first signal for notifying an emotion of the first user from the first mobile terminal 300A. However, it is apparent that a device except the second mobile terminal 300B or the second mobile terminal 400B can receive the first signal.

The controller 180 of the second mobile terminal 300B or the second mobile terminal 400B can output data for notifying an emotion of a first user on a display unit 351 or a display unit 451 based on the received first signal. Referring to FIGS. 12 (a) and (b), the controller 180 of the second mobile terminal 300B or the second mobile terminal 400B activates the camera 121 in response to the received first signal and can display a preview image 1210 obtained by the activated camera 121 on the display unit 351 or the display unit 451.

The controller 180 of the second mobile terminal 300B or the second mobile terminal 400B can display information 1230 corresponding to the first user on the preview image 1220. In addition, the controller 180 of the second mobile terminal 300B or the second mobile terminal 400B can display a capture command UI 1240 corresponding to a capture command on the preview image 1220. The controller 180 of the second mobile terminal 300B or the second mobile terminal 400B can capture the preview image 1220 according to a command for selecting the capture command UI 1240.

In FIG. 12, although an example of outputting the preview image 1210 on the display unit 351/451 according to the first signal is explained, the data mentioned earlier with reference to FIGS. 11 (a) and (c) can also be output on the display unit 351/451.

Figure 13:
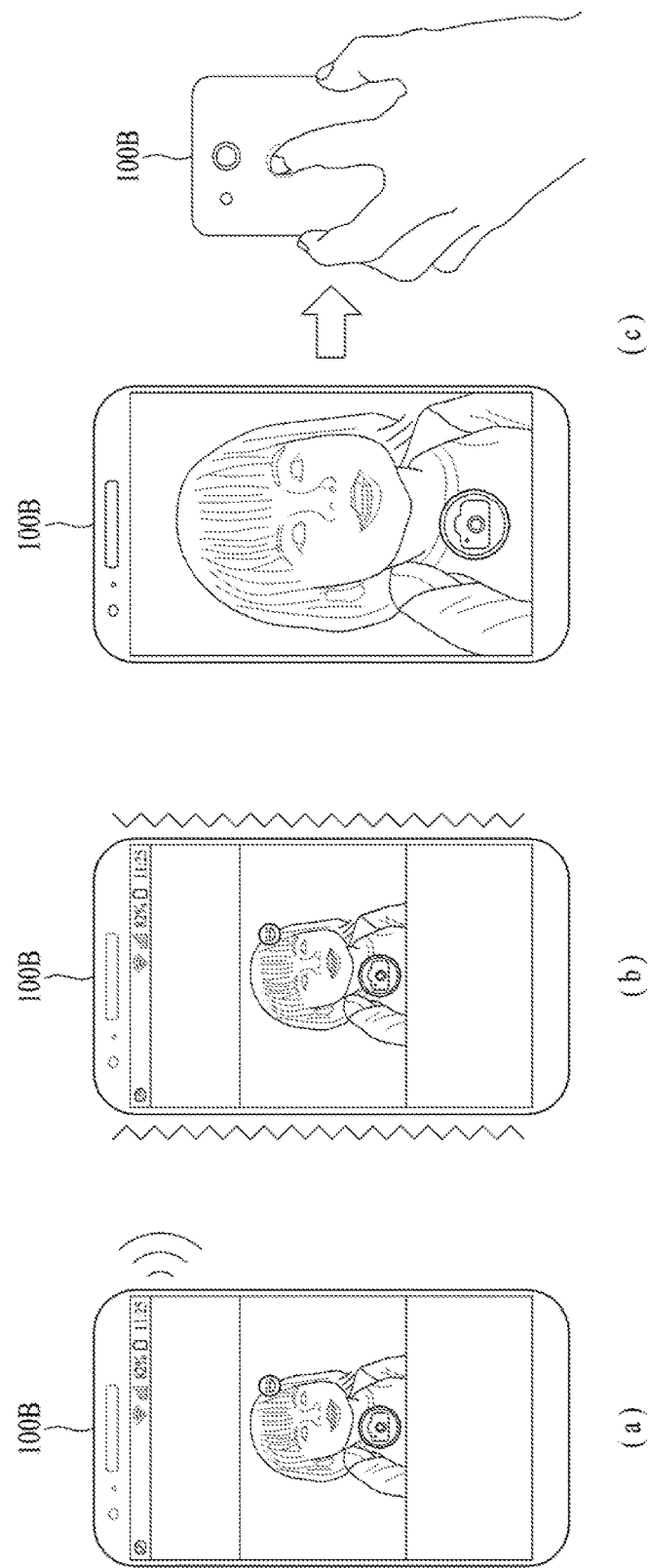
FIG. 13 is a diagram illustrating a second mobile terminal, which has received notification for emotion of a first user from a first mobile terminal, according to still another embodiment of the present invention.

Next, FIG. 13 is a diagram illustrating a second mobile terminal, which has received notification for the emotion of a first user from a first mobile terminal, according to another embodiment of the present invention. In the present embodiment, assume that the second mobile terminal 100B receives the first signal for notifying the emotion of the first user from the first mobile terminal 300A. However, it is apparent that a device except the second mobile terminal 100B can receive the first signal.

The controller 180 of the second mobile terminal 100B can output data for notifying an emotion of a first user on at least one of the display unit 151, the audio output module 152, the haptic module 153 and the optical output module 154. As an example, referring to FIG. 13 (a), the controller 180 of the second mobile terminal 100B can output predetermined audio data for notifying the emotion of the first user via the audio output module 152 in response to the received first signal. In this instance, the controller 180 of the second mobile terminal 100B can output the visual data mentioned earlier with reference to FIG. 11 on the display unit 151 together with the predetermined audio data.

As a different example, referring to FIG. 13 (b), the controller of the second mobile terminal 100B can output predetermined vibration data for notifying the emotion of the first user via the haptic module 153 in response to the received first signal. In this instance, the controller 180 of the second mobile terminal 100B can output the visual data mentioned earlier with reference to FIG. 11 on the display unit 151 together with the predetermined vibration data.

Further, referring to FIG. 13 (c), if a predetermined signal is detected in the middle of outputting data for notifying the emotion of the first user via the output unit 150, the controller 180 of the second mobile terminal 100B can stop outputting the data. As an example, the predetermined signal can be detected when a value of data for at least one of movement and a slope of the second mobile terminal 100B exceeds a predetermined value based on data sensed by the sensing unit 140 of the second mobile terminal 100B. If a second user of the second mobile terminal 100B checks the notification for the emotion of the first user, the second user can stop the notification by shaking the second mobile terminal 100B or flipping over the second mobile terminal 100B.

Further, according to one embodiment of the present invention, having received the notification for the emotion of the first user, the second user can deliver the notification to a user of a different external device, if it is determined in advance. This will be explained with reference to FIG. 14 in the following.

Figure 14:
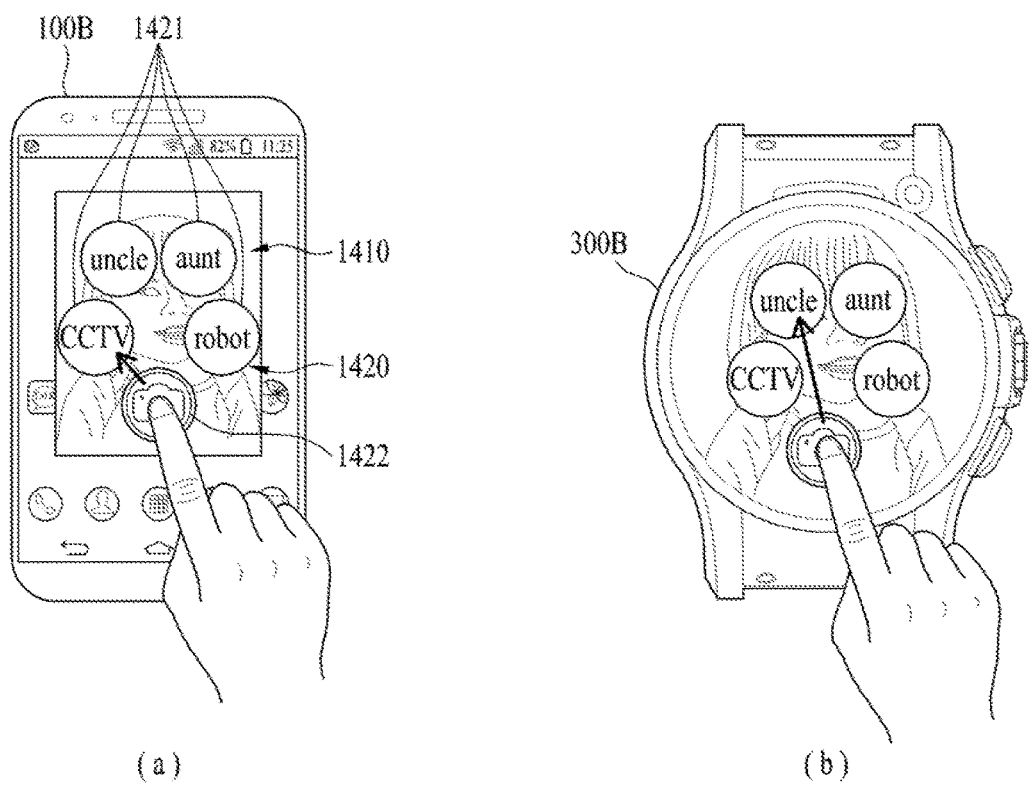
FIG. 14 is a diagram illustrating a method for a second mobile terminal, which has received notification for emotion of a first user from a first mobile terminal, to deliver the notification to a different external device according to one embodiment of the present invention.

FIG. 14 is a diagram illustrating a method for a second mobile terminal, which has received notification for emotion of a first user from a first mobile terminal, to deliver the notification to a different external device according to one embodiment of the present invention.

Referring to FIG. 14 (a), if a first signal for notifying an emotion of a first user is received from a first mobile terminal 300A, the controller 180 of the second mobile terminal 100B can output data 1410 for notifying the emotion of the first user on the display unit 151. In the present embodiment, if a predetermined condition is satisfied, the data 1410 can include a menu option 1420 for delivering a notification corresponding to the first signal to a different external device.

In this instance, the predetermined condition may correspond to a predetermined application (e.g., a phone call application, a video playback application, a DMB application etc.) is executed in the second mobile terminal 100B when the first signal is received, location information obtained via the location information module 115 of the second mobile terminal 100B corresponds to predetermined location information (e.g., a company, a library etc.) when the first signal is received, a notification mode of the second mobile terminal 100B is set to a manner mode, a command corresponding to a function predetermined by the second user is selected when the data mentioned earlier with reference to FIG. 11 is displayed on the display unit 151 or the like.

For instance, the menu option 1420 can include icons 1421 respectively corresponding to each of different external devices configured to deliver the notification corresponding to the first signal. If an icon 1421 of a specific external device is selected from the external devices corresponding to the icons 1421, the second user of the second mobile terminal 100B can deliver the notification corresponding to the first signal to the specific external device.

The menu option 1420 can further include an icon 1422 corresponding to a camera application. For example, the controller 180 of the second mobile terminal 100B can control the wireless communication unit 110 to deliver the notification corresponding to the first signal to the specific external device in response to a touch input selecting the icon 1422 and dragging the icon to the icon 1421 of the specific external device among the external devices corresponding to the icons 1421.

Since FIG. 14 (*a*) and FIG. 14 (*b*) are similar to each other except that a type of a second mobile terminal 300B shown in FIG. 14 (*b*) is different from a type of the second mobile terminal 100B, explanation on FIG. 14 (*b*) is omitted. In FIG. 14, although it is explained as a second mobile terminal 200B/300B delivers the first signal to a different external device, if the predetermined condition is satisfied, the second mobile terminal 200B/300B can transmit a third signal for notifying the predetermined condition to a first mobile terminal 300A and the first mobile terminal 300A can transmit the first signal to a predetermined different external device in response to the third signal.

Further, according to one embodiment of the present invention, if the second mobile terminal 100B receives a first signal for emotion of a first user of the first mobile terminal 300A, a picture of the first user can be taken without a separate capture command of a second user of the second mobile terminal 100B. This will be described with reference to FIG. 15 in the following.

Figure 15:
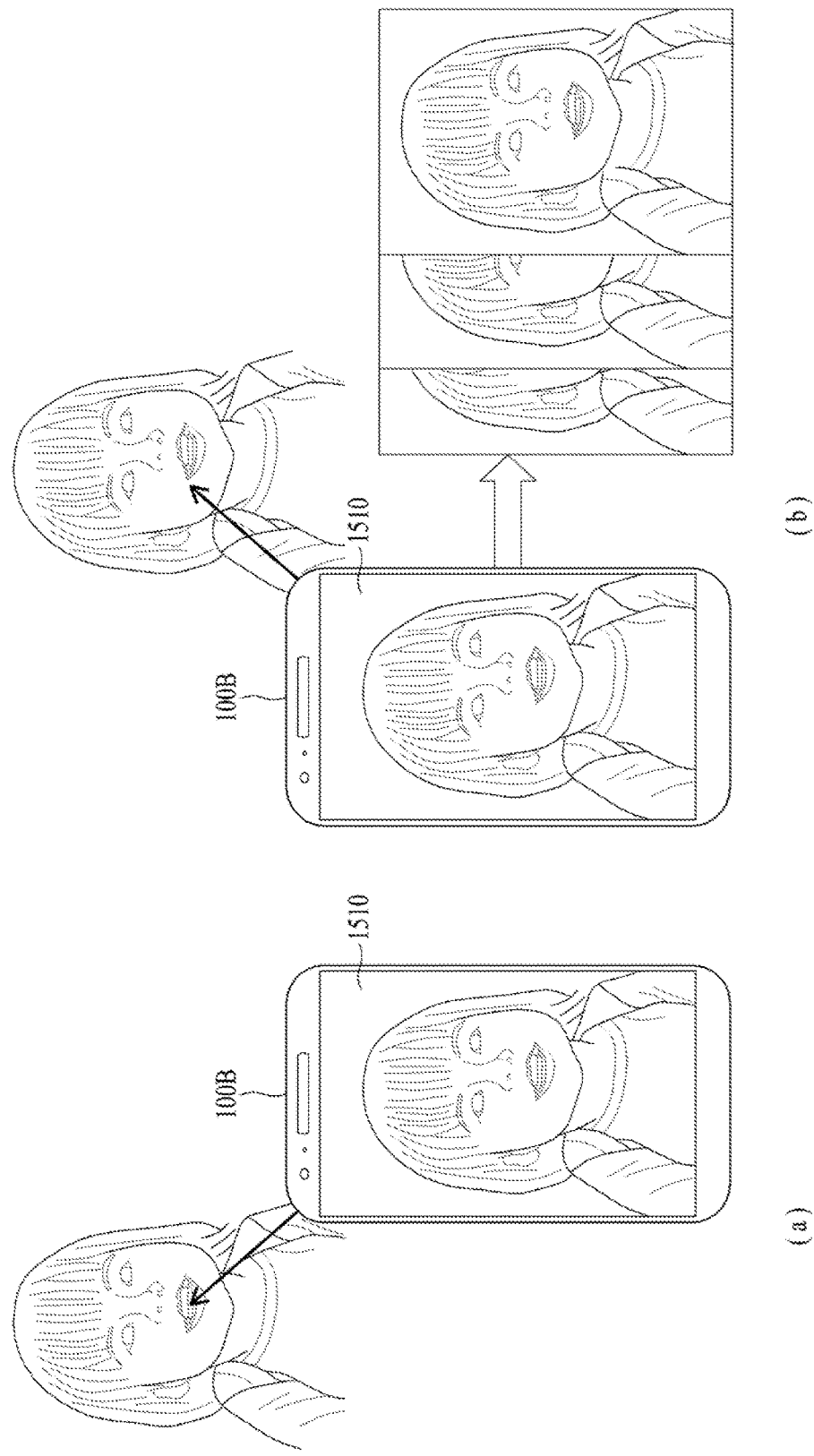
FIG. 15 is a diagram illustrating a method for a second mobile terminal, which has received notification for emotion of a first user from a first mobile terminal, to take a picture of the first user according to one embodiment of the present invention.

In particular, FIG. 15 is a diagram illustrating a method for a second mobile terminal, which has received notification for emotion of a first user from a first mobile terminal, to take a picture of the first user according to one embodiment of the present invention. Referring to FIG. 15 (*a*), if a first signal for notifying an emotion of a first user of a first mobile terminal 300A is received, the controller 180 of the second mobile terminal 100B activates the camera 121 and can display a preview image 1510 obtained by the activated camera 121 on the display unit 151.

In addition, the controller 180 of the second mobile terminal 100B can control the camera 121 to capture the preview image 1510 according to a predetermined condition without a capture command of a second user. Specifically, the sensing unit 1410 of the second mobile terminal 100B can obtain information (information on at least one of movement and a slope) of the second mobile terminal 100B. Subsequently, if the second mobile terminal 100B satisfies a predetermined condition, the controller 180 of the second mobile terminal 100B can control the camera 121 to capture a preview image based on the received first signal and data sensed by the sensing unit 140.

As an example, the predetermined condition can include that a value of data for the movement of the second mobile terminal 100B obtained by the sensing unit 140 is within a predetermined range when the second mobile terminal 100B faces direction to which the first signal is transmitted. In particular, if the second user holds the second mobile terminal 100B toward the first mobile terminal 300A for prescribed time, a picture can be automatically captured.

Further, referring to FIG. 15 (*b*), the controller 180 of the second mobile terminal 100B can control the camera 121 to capture the preview image 1510 many times with a constant interval according to a predetermined condition without a capture command of the second user. For example, if a data value for movement of the second mobile terminal 100B obtained by the sensing unit 140 is within a predetermined range when the second mobile terminal 100B faces direction to which the first signal is transmitted, the controller 180 of the second mobile terminal 100B captures the preview image one time. Subsequently, if movement of the second mobile terminal 100 moving in predetermined direction is detected, the controller 180 of the second mobile terminal 100B can control the camera 121 to continuously capture the preview image 1510 many times.

Further, according to one embodiment of the present invention, when capturing a picture of a first user using the second mobile terminal 100B, data for attracting attention of the first user is output via a first mobile terminal 300A. This will be explained with reference to FIG. 16 in the following.

Figure 16:
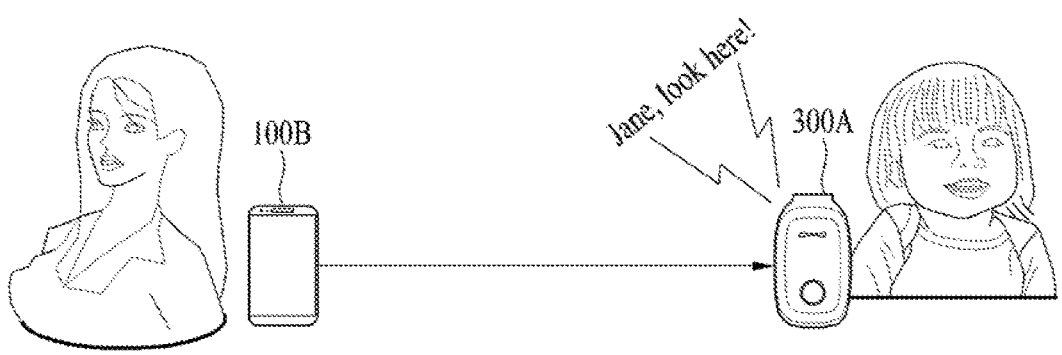
FIG. 16 is a diagram illustrating a method of outputting data for attracting attention of a first user via a first mobile terminal in case of taking a picture of the first user using a second mobile terminal according to one embodiment of the present invention.

In particular, FIG. 16 is a diagram illustrating a method of outputting data for attracting attention of a first user via a first mobile terminal when taking a picture of the first user using a second mobile terminal according to one embodiment of the present invention.

If a notification for emotion of a first user is received from the first mobile terminal 300A, the controller 180 of the second mobile terminal 100B can control the wireless communication unit 110 to transmit predetermined audio data to the first mobile terminal 300A. For example, if a specific command is detected, the controller 180 of the second mobile terminal 100B activate the microphone 122 and can obtain audio data corresponding to voice of a second user via the microphone 122.

Subsequently, the controller 180 of the second mobile terminal 100B can transmit the obtained audio data to the first mobile terminal 300A via the wireless communication unit 110. The specific command can be detected when a prescribed menu corresponding to a function of recording the voice is selected. The second user records voice of the second user to attract attention of the first user when the second user captures a picture of the first user using the second mobile terminal 100B and can make audio data corresponding to the recorded voice to be played in the first mobile terminal 300A.

Figure 17:
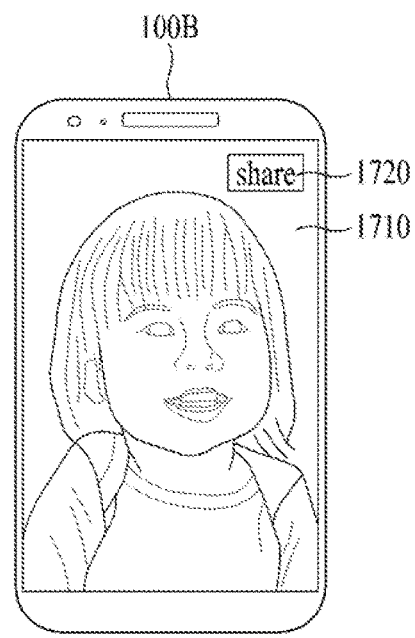
FIG. 17 is a diagram illustrating a method of sharing a captured picture with an external device in case of taking a picture of a first user using a second mobile terminal according to one embodiment of the present invention.

FIG. 17 is a diagram illustrating a method of sharing a captured picture with an external device in case of taking a picture of a first user using a second mobile terminal according to one embodiment of the present invention. Referring to FIG. 17, an image 1710 of which a first user of a first mobile terminal 300A is captured is displayed on the display unit 151 of the second mobile terminal 100B.

If a picture is taken (image capture) via the camera 121 according to reception of a notification for emotion of the first user received from the first mobile terminal 300A, the controller 180 of the second mobile terminal 100B can output the captured picture (image) 1710 on the display unit 151. Subsequently, the controller 180 of the second mobile terminal 100B can automatically display GUI 1710 corresponding to a menu option for sharing the captured picture 1710 with a predetermined external device on the display unit 151.

In addition, the controller 180 of the second mobile terminal 100B can display information on an external device capable of sharing the picture 1710 on the display unit 151 according to a command for selecting the GUI 1720. For example, the external device capable of sharing the picture 1710 may correspond to an external device of which short-range communication is established with the second mobile terminal 100B, a predetermined external device configured to receive a notification when the first user of the first mobile terminal 300A shows specific emotion, a predetermined external device, which has received a notification when the first user of the first mobile terminal 300A has shown specific emotion, and the like.

Figure 18:
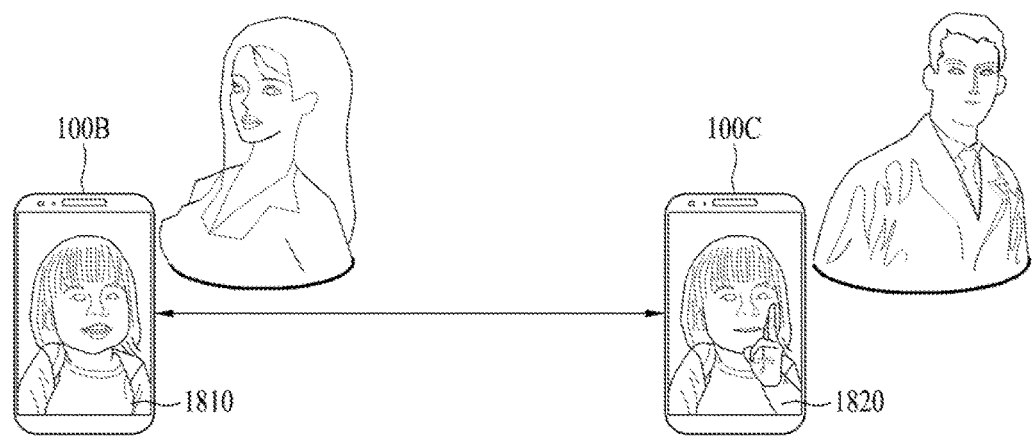
FIG. 18 is a diagram illustrating explaining a method of sharing a captured picture with an external device in case of taking a picture of a first user using the external device according to a different embodiment of the present invention.

Next, FIG. 18 is a diagram illustrating a method of sharing a captured picture with an external device when taking a picture of a first user using the external device according to one embodiment of the present invention. In the present embodiment, assume that a first signal for notifying an emotion of a first user of a first mobile terminal 300A is received by a second mobile terminal 100B and a third mobile terminal 100C.

A second user of the second mobile terminal 100B can take a picture of the first user using the camera 121. If a capture command of a user is detected or the predetermined condition mentioned earlier with reference to FIG. 15 is satisfied, the controller 180 of the second mobile terminal 100B obtains a first image 1810 and can store the obtained first image 1810 in the memory 170. Subsequently, the controller 180 of the second mobile terminal 100B can transmit a first signal including the first image 1810 to a predetermined third mobile terminal 100C via the wireless communication unit 110 without a separate user request.

The third mobile terminal 100C corresponds to the predetermined mobile terminal configured to receive a notification for the emotion of the first user. The second mobile terminal 100B can store information on the predetermined mobile terminal configured to receive the notification for the emotion of the first user in the memory 170 in advance. The controller 180 of the third mobile terminal 100C can automatically store the first image 1810 included in the first signal in the memory 170.

Further, a third user of the third mobile terminal 100C can take a picture of the first user using the camera 121. If a capture command of a user is detected or the predetermined condition mentioned earlier with reference to FIG. 15 is satisfied, the controller 180 of the third mobile terminal 100C obtains a second image 1820 and can store the obtained second image 1820 in the memory 170. Subsequently, the controller 180 of the third mobile terminal 100C can transmit a second signal including the second image 1820 to the predetermined second mobile terminal 100B via the wireless communication unit 110 without a separate user request.

The second mobile terminal 100B corresponds to the predetermined mobile terminal configured to receive a notification for the emotion of the first user. The third mobile terminal 100B can store information on the predetermined mobile terminal configured to receive the notification for the emotion of the first user in the memory 170 in advance. The controller 180 of the second mobile terminal 100B can automatically store the second image 1820 included in the second signal in the memory 170. In particular, according to the present embodiment, a picture captured by each mobile terminal can be automatically shared between predetermined mobile terminals configured to receive a notification for emotion of the first user.

Figure 19:
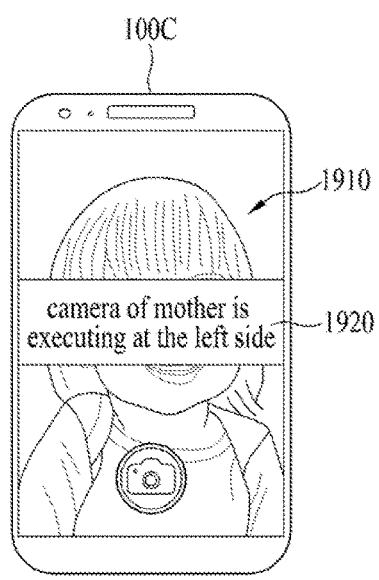
FIG. 19 is a diagram illustrating a method of sharing information between external devices, which have received a notification for emotion of a first user, according to one embodiment of the present invention.

FIG. 19 is a diagram illustrating a method of sharing information between external devices, which have received a notification for emotion of a first user, according to one embodiment of the present invention. The controller 180 of the first mobile terminal 300A can transmit a first signal for notifying specific emotion of a first user to a predetermined second mobile terminal 100B and a third mobile terminal 100C via the wireless communication unit 100C.

Subsequently, the controller 180 of the second mobile terminal 100B and the controller of the third mobile terminal 100C receive the first signal via the wireless communication unit 110 and can output data 1910 for notifying the emotion of the first user on the display unit 151. Since the data 1910 is similar to what is mentioned earlier with reference to FIG. 11, detail explanation on the data is omitted at this time.

If a prescribed operation is performed in each of the mobile terminals in response to the first signal, a second signal including mutual status information can be transceived between the mobile terminals. In the present embodiment, an example for a case that the third mobile terminal 100C receives the second signal from the second mobile terminal 100B is explained.

The controller 180 of the third mobile terminal 100C can control the wireless communication unit 110 to receive the second signal including status information of the second mobile terminal 100B. For example, if the camera 121 is executed after the first signal is received, the controller 180 of the second mobile terminal 100B can transmit the second signal including information indicating that the camera 121 is executed to the third mobile terminal via the wireless communication unit 110.

The controller 180 of the third mobile terminal 100C can output a message 1920 corresponding to status information of the second mobile terminal 100B on the display unit 15 based on information included in the received second signal. For example, the message 1920 can include information on a second user of the second mobile terminal 100B, information on a relative position of the second mobile terminal 100B based on a front side of the third mobile terminal 100C based on direction to which the second signal is transmitted and execution information of the camera 121 of the second mobile terminal 100B. According to an embodiment of the present invention, a third user of the third mobile terminal 100C can determine whether to take a picture of the first user, direction from which a picture is taken, and the like based on current status of the second user.

In the following, embodiments of providing a notification for emotion of a first user to an external device by a plurality of first mobile terminals 300A are explained with reference to FIG. 20 and FIG. 21. In particular, FIG. 20 is a diagram illustrating a method for a plurality of first mobile terminals to provide a notification for emotion of a first user to an external device according to one embodiment of the present invention.

Figure 20:
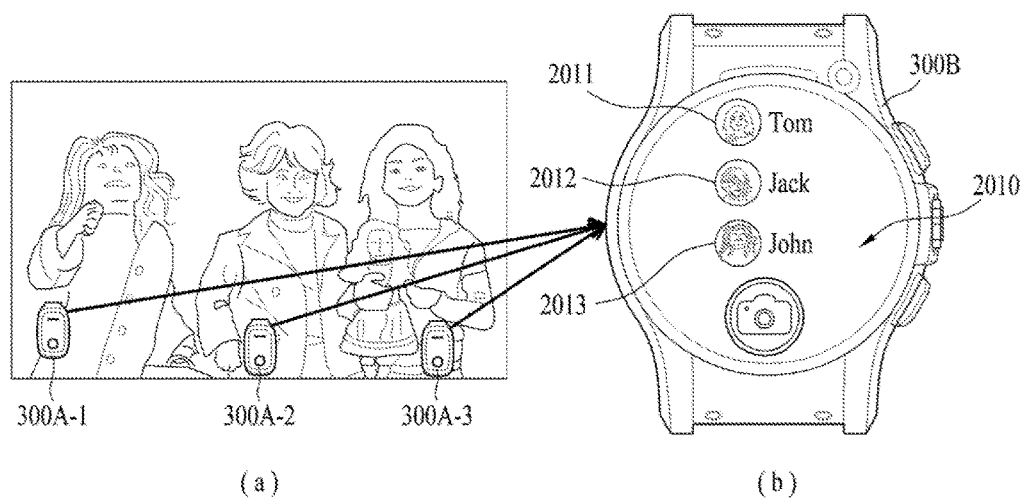
FIG. 20 is a diagram illustrating a method for a plurality of first mobile terminals to provide a notification for emotion of a first user to an external device according to one embodiment of the present invention.

Referring to FIG. 20 (a), there are three first users and each of the first users is wearing a first mobile terminal 300A-1/300A-2/300A-3. The controller 180 of each of the first mobile terminals 300A-1/300A-2/300A-3 recognizes the emotion of the first user based on data sensed by the sensing unit 140. If the sensed emotion corresponds to a predetermined emotion, the controller controls the wireless communication unit 110 to transmit a first signal for notifying the emotion of the first user to a second mobile terminal 300B.

Referring to FIG. 20 (b), the controller 180 of the second mobile terminal 300B outputs data for notifying the emotion of each of the first users on the display unit 351 in response to the first signal received from the each of the first mobile terminals 300A-1/300A-2/300A-3. In the present embodiment, if the first signals are practically received from the each of the first mobile terminals 300A-1/300A-2/300A-3 at the same time, the controller 180 of the second mobile terminal 300B can display data 2010 for notifying an emotion of the three first users on the display unit 351 together based on information included in the three first signals. The three first signals practically received at the same time may indicate that the three first signals are received within a predetermined time range.

The data 2010 output on the display unit 351 can include information 2011 to 2013 on each of the three first users. For instance, the information 2011 to 2013 on each of the three first users can include information for identifying a first user and information 2011 for indicating current emotion of the first user, information for identifying a second first user and information 2012 for indicating current emotion of the second first user and information for identifying a third first user and information 2013 for indicating current emotion of the third first user. Because explanation on the data 2010 is similar to what is mentioned earlier with reference to FIG. 11 and FIG. 12, detail explanation on the data is omitted at this time.

Figure 21:
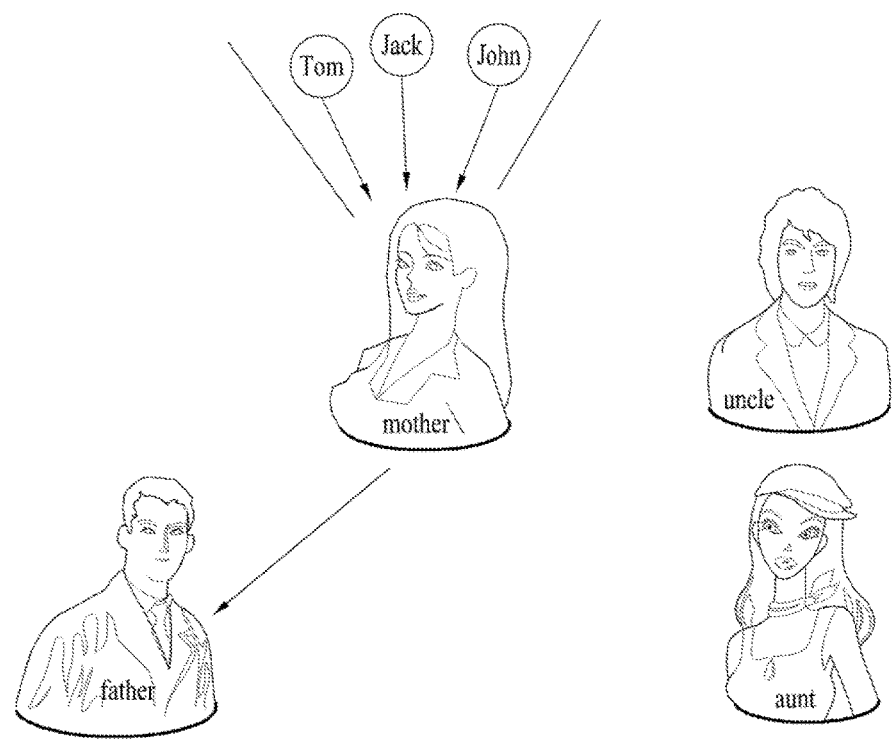
FIG. 21 is a diagram illustrating a method for a plurality of first mobile terminals to provide a notification for emotion of a first user to an external device according to one embodiment of the present invention.

FIG. 21 is a diagram illustrating a method for a plurality of first mobile terminals to provide a notification for emotion of a first user to an external device according to another embodiment of the present invention.

When there is a plurality of external devices capable of receiving a first signal for notifying an emotion of a first user from each first mobile terminal 300A of a plurality of first users, the present embodiment may correspond to an example for an external device to which the first signal is transmitted. The controller 180 of each of the first mobile terminals 300A-1/300A-2/300A-3 recognizes the emotion of a first user based on data sensed by the sensing unit 140.

If the recognized emotion corresponds to a predetermined emotion, the controller controls the wireless communication unit 110 to transmit a first signal for notifying the emotion of the first user to a predetermined external device. In this instance, the controller 180 of each of the first mobile terminals 300A-1/300A-2/300A-3 transmits a prescribed signal to each external device before the first signal is transmitted to the predetermined external device and can identify direction at which each external device is located based on a second signal received from each external device.

In addition, the first mobile terminals 300A-1/300A-2/300A-3 are connected with each other via short range communication and may be aware of a mutual location relation based on a signal transceived with each other. The controller 180 of each of the first mobile terminals 300A-1/300A-2/300A-3 can control the wireless communication unit 110 to transmit the first signal to a specific external device located at a position (direction) appropriate for capturing the three first users at a time.

As an example, the specific external device may correspond to a second mobile terminal 100B of a mother. When the specific external device located at the position (direction) appropriate for capturing the three first users at a time is determined, the controller 180 of each of the first mobile terminals 300A-1/300A-2/300A-3 may also consider viewing angle information of a camera of an external device. In this instance, each of the first mobile terminals 300A-1/300A-2/300A-3 may be aware of viewing angle information of a camera of each external device.

If the second mobile terminal 100B satisfies the predetermined condition mentioned earlier with reference to FIG. 14, the second mobile terminal 100B can deliver the received first signal to a predetermined different external device (e.g., a third mobile terminal 100C of a father).

Further, according to one embodiment of the present invention, in case of capturing a first user using a second mobile terminal 100B, it can recognize expression in a captured picture and may be then able to determine whether to receive a notification for emotion corresponding to the recognized expression in the future. Regarding this, it is explained with reference to FIG. 22 in the following.

Figure 22:
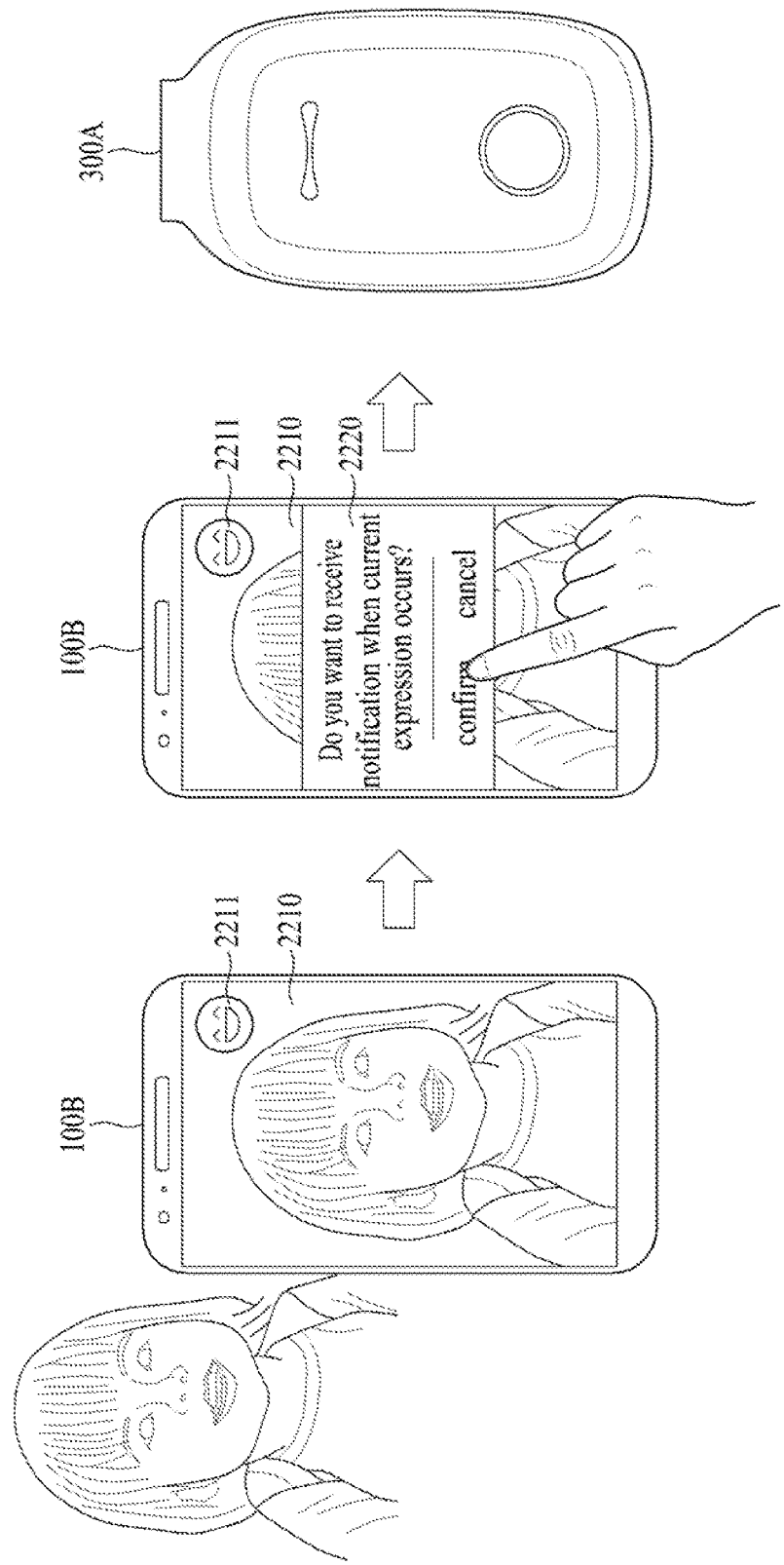
FIG. 22 is a diagram illustrating a method for a second mobile terminal to select whether to notify emotion corresponding to expression of a first user included in a captured picture in case of taking a picture of the first user using the second mobile terminal according to one embodiment of the present invention.

FIG. 22 is a diagram illustrating a method for a second mobile terminal to select whether to notify emotion corresponding to expression of a first user included in a captured picture in case of taking a picture of the first user using the second mobile terminal according to one embodiment of the present invention.

A second user of a second mobile terminal 100B can take a picture of a first user using the camera 121. The controller 180 of the second mobile terminal 100B obtains an image via the camera according to a picture capture command and can display the obtained image 2210 on the display unit 151. The picture capture command may occur in a manner that the second user executes a camera application in a general way and selects a capture menu irrespective of whether emotion of the first user is notified. Alternatively, the picture capture command may occur by the second user based on the notification for the emotion of the first user or may automatically occur as mentioned earlier with reference to FIG. 15. The image 2210 may correspond to a preview image obtained by the camera 121 without a capture command.

The controller 180 of the second mobile terminal 100B recognizes a face of the first user included in the image 2210 and can recognize expression of the recognized face. The memory 170 of the second mobile terminal 100B can store a program/algorithm for recognizing a face and expression in advance. In addition, the controller 180 of the second mobile terminal 100B can identify the first user via face recognition and the memory 170 can store information on a first mobile terminal 300A of the first user in advance.

The controller 180 of the second mobile terminal 100B can display an indicator 2211 corresponding to the recognized expression on the display unit 151. For example, the indicator 221 may correspond to an indicator indicating smile expression, sad expression, angry expression, scared expression or the like.

The controller 180 of the second mobile terminal 100B can display GUI 2220 for checking whether to notify emotion corresponding to the recognized expression on the display unit 151. If the first user shows the emotion corresponding to the recognized expression via the GUI 2220, the second user can determine whether to receive a notification for the emotion corresponding to the recognized expression.

The controller 180 of the second mobile terminal 100B can transmit a signal including information on the emotion corresponding to the recognized expression to the first mobile terminal 300A of the first user according to a command for selecting a confirm menu in the GUI 2220. The controller 180 of the first mobile terminal 300A stores the information on the emotion corresponding to the recognized expression in the memory 170 based on the signal. If it is determined that the emotion of the first user corresponds to the emotion corresponding to the recognized expression based on data sensed by the sensing unit 140, the controller of the first mobile terminal can transmit a signal for notifying the emotion of the first user to the second mobile terminal 100B.

Further, according to one embodiment of the present invention, when providing a notification for emotion of a first user to an external device, many conditions can be configured in advance. This will be explained with reference to FIG. 23 in the following.

Figure 23:
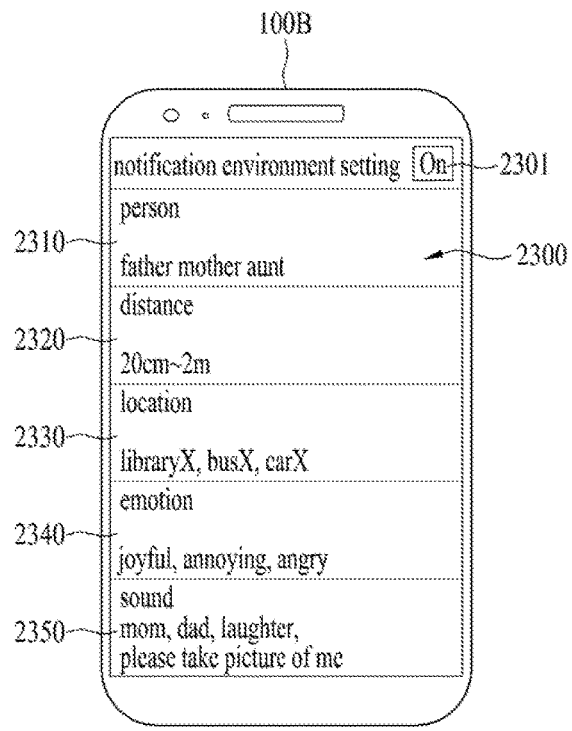
FIG. 23 is a diagram illustrating a method for a mobile terminal to configure a condition for providing a notification for emotion of a first user to an external device according to one embodiment of the present invention.

In particular, FIG. 23 is a diagram illustrating a method for a mobile terminal to configure a condition for providing a notification for emotion of a first user to an external device according to one embodiment of the present invention. In the present embodiment, assume that the aforementioned condition is configured by a second mobile terminal 100B of a second user corresponding to a guardian of a first user and information on the configured condition is transmitted to a first mobile terminal 300A.

However, it is possible to configure the aforementioned condition by the first mobile terminal 300A itself. In the latter case, an environment setting interface 2300 to be mentioned later can be displayed on the display unit 351 of the first mobile terminal 300A. The controller 180 of the second mobile terminal 100B can display the environment setting interface 2300 of a notification function for emotion on the display unit 151 according to a command for selecting a menu for configuring environment of a notification function for emotion of a specific person (e.g., first user).

The environment setting interface 2300 can include a menu option 2310 for selecting whether to activate an emotion notification function of a first user. If the emotion notification function of the first user is activated by the menu option 2301, various menu options described in the following can also be activated and displayed.

The environment setting interface 2300 can include at least one of a first menu option 2310 for selecting an external device configured to receive a signal for notifying an emotion of the first user, a second menu option 2320 for limiting an external device to external devices located within a prescribed distance from the first mobile terminal 300A when a signal for emotion of the first user is transmitted to an external device, a third menu option 2330 for making the signal not to be transmitted to an external device located at the inside of a predetermined place when the signal for emotion of the first user is transmitted to an external device and a fourth menu option 2340 for selecting a type of emotion of the first user to be informed to an external device.

Also, if predetermined audio data is included in voice spoken by the first user, the environment setting interface 2300 can further include a fifth menu option 2350 to provide a notification to an external device irrespective of specific emotion of the first user. For example, if the microphone 122 is activated and predetermined audio data (audio data corresponding to sound of laughter, audio data corresponding to a specific word, etc.) is included in a voice signal obtained by the activated microphone 122, the controller 180 of the first mobile terminal 300A can provide a notification for inducing picture capturing of the first user to a predetermined external device.

Figure 24:
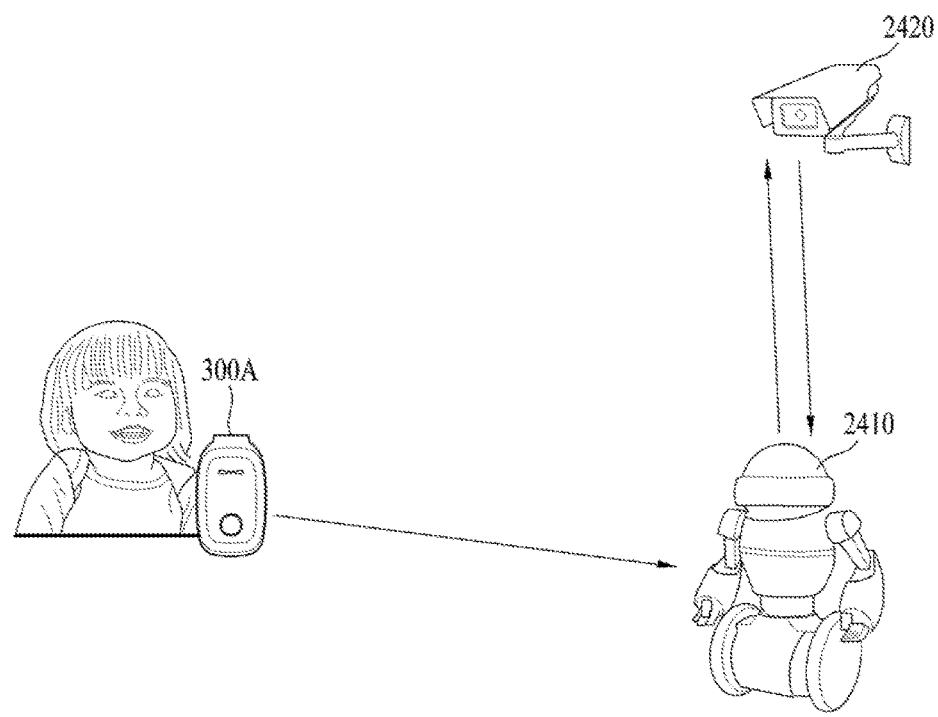
FIG. 24 is a diagram illustrating a method of taking a picture of a first user using a different external device positioned at home according to one embodiment of the present invention when a user of a predetermined external device configured to receive a notification for a specific event occurred to the first user is not at home.

In the following, if a specific event occurs to a first user but a user of a predetermined device configured to receive a notification for the event is not at home, an example for a method of capturing the first user using a different external device in the home is explained with reference to FIG. 24 to FIG. 26. In particular, FIG. 24 is a diagram illustrating a method of taking a picture of a first user using a different external device positioned at home according to one embodiment of the present invention when a user of a predetermined external device configured to receive a notification for a specific event occurred to the first user is not at home.

If the first user shows specific emotion based on data sensed by the sensing unit 140, the controller 180 of the first mobile terminal 300A can transmit a first signal for notifying the emotion of the first user to a predetermined external device. However, in this instance, if it is determined that a distance to the predetermined external device is equal to or greater than a predetermined level, the controller 180 of the first mobile terminal 300A can provide the first signal to an external device positioned at home instead of the predetermined external device. The controller 180 of the first mobile terminal 300A can determine that the distance to the predetermined external device is equal to or greater than the predetermined level based on short range communication not established with the predetermined external device or location information received from the predetermined external device.

As an example, if it is determined that the distance to the predetermined external device is equal to or greater than the predetermined level, the controller 180 of the first mobile terminal 300A can provide a notification to an electronic robot 2410 positioned at home. If a camera is mounted on the electronic robot, the electronic robot 2410 activates the camera and may be then able to take a picture of the first user. If a camera is not mounted on the robot, the notification can be delivered to a different device (e.g., a CCTV 2420) to which a camera is mounted positioned at home. The CCTV 2420 can store an image (video) obtained by the camera in a memory according to the notification.

Figure 25:
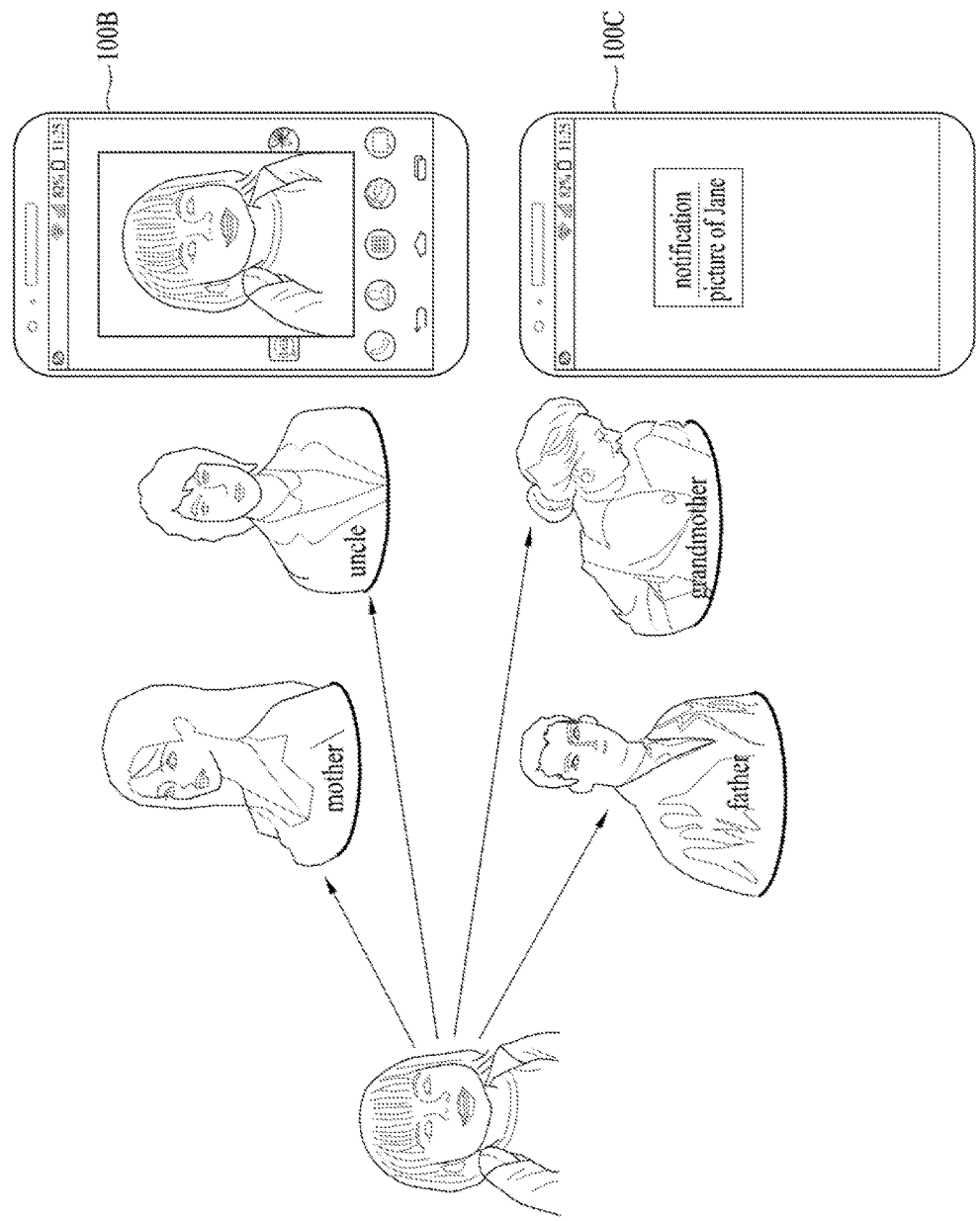
FIG. 25 is a diagram illustrating a method of sharing an image captured by a device positioned at home, which is mentioned earlier in FIG. 24, with a predetermined external device.

FIG. 25 is a diagram illustrating a method of sharing an image captured by a device positioned at home, which is mentioned earlier in FIG. 24, with a predetermined external device. In the embodiment of FIG. 24, the image obtained via the electronic robot 2410 and/or the CCTV 2420 positioned at home can be shared between predetermined external devices (e.g., a second external device 100B and a third external device 100C).

If the electronic robot 2410 and/or the CCTV 2420 are equipped with a communication module, the electronic robot 2410 and/or the CCTV 2420 can directly transmit the image to a predetermined external device. Alternatively, the electronic robot 2410 and/or the CCTV 2420 transmit the image to the first mobile terminal 300A and the first mobile terminal 300A may be then able to deliver the image to the predetermined external device.

As an example, if the display unit 151 is in a state of being turned on when the image is received, the controller 180 of the second mobile terminal 100B can display the received image on the display unit 151. As a different example, if the display unit 151 is in a state of being turned off when the image is received, the controller 180 of the third mobile terminal 100C can display a notification message notifying that the image of the first user is received on the display unit 151.

Figure 26:
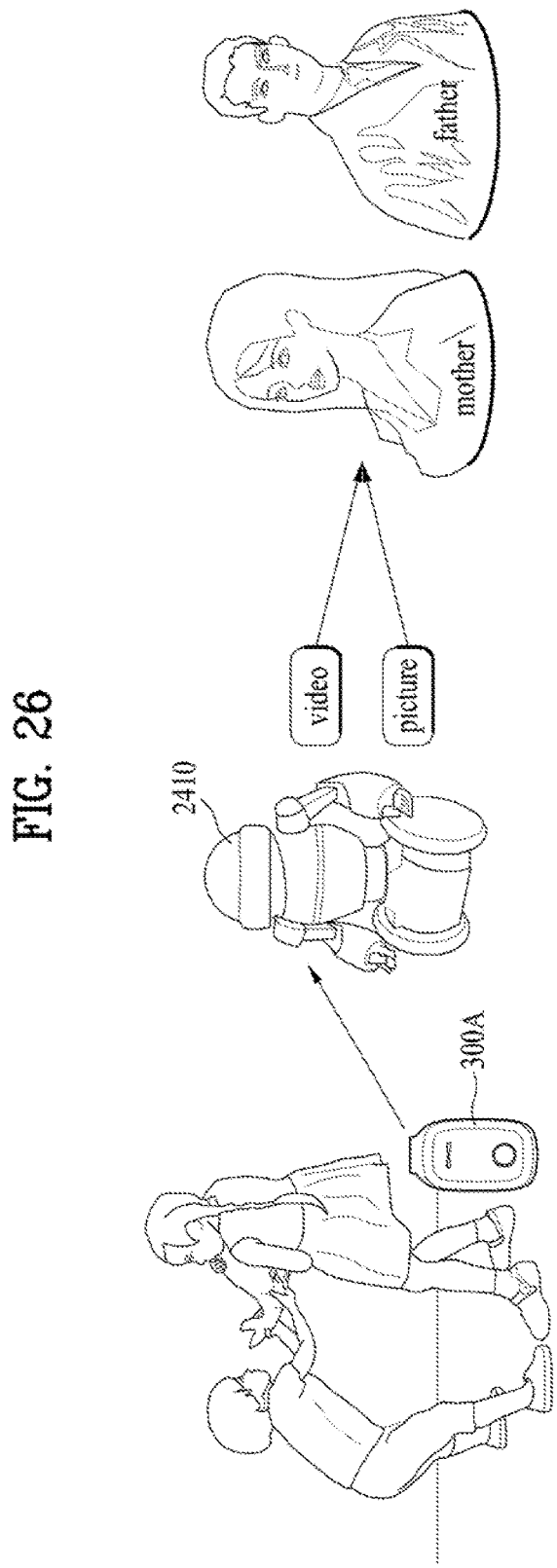
FIG. 26 is a diagram illustrating a method of taking a picture of a first user using a different external device positioned at home according to one embodiment of the present invention when a user of a predetermined external device configured to receive a notification for a specific event occurred to the first user is not at home.

FIG. 26 is a diagram illustrating a method of taking a picture of a first user using a different external device positioned at home according to one embodiment of the present invention when a user of a predetermined external device configured to receive a notification for a specific event occurred to the first user is not at home.

If negative emotion occurs to a first user, the controller 180 of the first mobile terminal 300A can provide a notification to an electronic device (e.g., an electronic robot 2410) positioned at home based on data sensed by the sensing unit 1410. If a camera is installed in the electronic robot, the electronic robot 2410 can take a picture of the first user by activating the camera according to the notification. If a camera is not installed in the robot, the notification can be delivered to a different device (not depicted) to which a camera is mounted positioned at home. The electronic robot 2410 and/the CCTV can store an image (video) obtained by the camera in the memory.

Subsequently, the obtained image can be transmitted to a predetermined external device (e.g., a mobile terminal of a mother and a mobile terminal of a father). As mentioned earlier with reference to FIG. 25, the image can be transmitted to the predetermined external device by the electronic robot 2410 and/or the CCTC 2420 or can be transmitted to the predetermined external device via the first mobile terminal 300A.

According to the aforementioned embodiments of the present invention, a mobile terminal is provided enabling a guardian to take an appropriate step by providing a notification according to emotion of a ward to the guardian. In addition, a mobile terminal is provided capable of immediately taking a picture of a ward without missing a shape of the ward when the ward (i.e., child) shows a specific emotion. In addition, a mobile terminal is provided capable of easily sharing a picture of a ward (i.e., children) with a different device.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A mobile terminal, comprising:
a wireless communication processor configured to receive a signal from a first external device notifying an emotional state of a first user of the first external device;
a sensor configured to sense at least one of a movement and a slope of the mobile terminal;
a display;
a camera; and
a controller configured to:
activate the camera and display a preview image obtained by the activated camera, in response to the emotional state of the first user being a specific emotional state,
control the camera to capture the preview image in response to a predetermined condition, wherein the predetermined condition is determined based on the signal from the first external device and at least one of the movement and the slope of the mobile terminal, and
display an execution screen of an application on a first area of the display and display the preview image on a second area of the display when the signal from the first external device is received while the application is being executed on the mobile terminal.

2. The mobile terminal of claim 1, wherein the controller is configured to output information indicating the specific emotional state of the first user.

3. The mobile terminal of claim 1, further comprising:
an audio output module configured to output audio data indicating the specific emotional state of the first user, and
a haptic module configured to output vibration data indicating the specific emotional state of the first user.

4. The mobile terminal of claim 1, wherein the controller is configured to display information corresponding to the first user on the display.

5. The mobile terminal of claim 1,
wherein the predetermined condition for capturing the preview image corresponds to the mobile terminal moving in a direction of the first user of the first external device.

6. The mobile terminal of claim 5, wherein the controller is configured to control the wireless communication processor to transmit the captured image to a predetermined second external device.

7. The mobile terminal of claim 5, wherein the controller is configured to control the camera to capture the preview image many times with a constant time interval.

8. The mobile terminal of claim 1, wherein the controller is configured to display a Graphic User Interface (GUI) on the display including a menu option for sharing the captured image with a predetermined second external device.

9. The mobile terminal of claim 1, wherein when the signal is received while the application is being executed on the mobile terminal, the controller is configured to display a Graphic User Interface (GUI) on the display indicating the emotional state of the first user including a menu option for notifying the emotional state of the first user to a predetermined external device.

10. The mobile terminal of claim 1, wherein the wireless communication processor is configured to receive status information of a second external device,
wherein the controller is configured to display data on the display corresponding to the status information, and
wherein the status information of the second external device comprises execution information of a camera mounted on the second external device.

11. The mobile terminal of claim 1, wherein the controller is configured to:
  recognize an expression of a face contained in the preview image or the captured image,
  display a Graphic User Interface (GUI) on the display for indicating whether to notify the emotional state corresponding to the recognized expression, and
  control the wireless communication processor to transmit an information signal containing information on the emotional state corresponding to the recognized expression to the first external device.

12. The mobile terminal of claim 1, wherein the emotional state of the first user is based on at least one of a heart rate, skin temperature, respiration volume and blood pressure of the first user.

* * * * *